US011220667B2

(12) United States Patent
Hu et al.

(10) Patent No.: US 11,220,667 B2
(45) Date of Patent: *Jan. 11, 2022

(54) BACTERIA FOR DEGRADING ETHYLENE OXIDE AND APPLICATIONS THEREOF

(71) Applicants: Chio Kang Medical, Inc., Palo Alto, CA (US); QIAOKANG BIOTECH (GUANGDONG) CO., LTD., Guangzhou (CN)

(72) Inventors: Shengwei Hu, Guangzhou (CN); Dongxin Hou, Guangzhou (CN); Jianlong Xue, Guangzhou (CN); Weiguo Wang, Guangzhou (CN); Yecheng He, Guangzhou (CN); Xiuling Zhong, Guangzhou (CN); Xin Yin, Guangzhou (CN); Liqing Zhu, Guangzhou (CN); Jiali Lin, Guangzhou (CN); Lixiong Feng, Guangzhou (CN)

(73) Assignees: CHiO KANG MEDICAL, INC., Palo Alto, CA (US); QIAOKANG BIOTECH (GUANGDONG) CO., LTD., Guangdong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/012,810

(22) Filed: Sep. 4, 2020

(65) Prior Publication Data
US 2021/0222119 A1   Jul. 22, 2021

Related U.S. Application Data

(63) Continuation of application No. PCT/CN2020/101138, filed on Jul. 9, 2020.

(51) Int. Cl.
*C12N 1/36*    (2006.01)
*C02F 3/34*    (2006.01)
(Continued)

(52) U.S. Cl.
CPC ............... *C12N 1/36* (2013.01); *B01D 53/72* (2013.01); *B01D 53/84* (2013.01); *C02F 3/341* (2013.01);
(Continued)

(58) Field of Classification Search
CPC .......... C12N 1/36; C12N 1/205; B01D 53/72; B01D 53/84; B01D 2251/95; C02F 3/341; C02F 2101/34; C12R 2001/145
See application file for complete search history.

(56) References Cited

U.S. PATENT DOCUMENTS 1,954,056 A   4/1934   Miller
2,586,670 A   2/1952   Lambertsen
(Continued)

FOREIGN PATENT DOCUMENTS

CN   1223166 A   7/1999
CN   1397474 A   2/2003
(Continued)

OTHER PUBLICATIONS

Bao, et al., (2010) Food Control, 21:695-701, "Screening of potential probiotic properties of Lactobacillus fermentum isolated from traditional dairy products".
(Continued)

*Primary Examiner* — David W Berke-Schlessel
*Assistant Examiner* — Trent R Clarke
(74) *Attorney, Agent, or Firm* — Adsero IP

(57) ABSTRACT

A *Kurthia gibsonii* strain EO-06 with Deposit Number of CGMCC No. 18436, a *Clostridium kogasensis* strain EO-08 with Deposit Number of CGMCC No. 18438 and a *Clostridium acidisoli* strain EO-09 with Deposit Number of CGMCC No. 18439 are provided. The above strains can be used to treat pollution, for example, to treat industrial gas or wastewater containing ethylene oxide, which greatly
(Continued)

improves the decontamination disposal capacity of ethylene oxide in industrial production. The present disclosure also provides a degradation agent for degrading ethylene oxide and a method for biodegrading ethylene oxide.

12 Claims, 8 Drawing Sheets

Specification includes a Sequence Listing.

(51) Int. Cl.
*B01D 53/84* (2006.01)
*B01D 53/72* (2006.01)
*C12N 1/20* (2006.01)
*C02F 101/34* (2006.01)
*C12R 1/145* (2006.01)

(52) U.S. Cl.
CPC .......... *C12N 1/205* (2021.05); *B01D 2251/95* (2013.01); *C02F 2101/34* (2013.01); *C12R 2001/145* (2021.05)

(56) References Cited

U.S. PATENT DOCUMENTS

| | | |
|---|---|---|
| 2,817,689 A | 12/1957 | White |
| 3,022,054 A | 2/1962 | Kotzebue |
| 3,572,391 A | 3/1971 | Hirsch et al. |
| 3,598,543 A | 8/1971 | Crosby et al. |
| 3,844,739 A | 10/1974 | Alfrey, Jr. |
| 3,961,920 A | 6/1976 | Gilbert |
| 3,997,633 A | 12/1976 | Leva et al. |
| 4,112,054 A | 9/1978 | Feingold et al. |
| 4,119,539 A | 10/1978 | Ettel et al. |
| 4,134,425 A | 1/1979 | Gussefeld et al. |
| 4,243,636 A | 1/1981 | Shiraki et al. |
| 4,274,954 A | 6/1981 | Blair |
| 4,301,113 A | 11/1981 | Alguire et al. |
| 4,517,167 A | 5/1985 | Popescu et al. |
| 4,549,363 A | 10/1985 | Buonicore |
| 4,831,196 A | 5/1989 | Buonicore et al. |
| 5,084,075 A | 1/1992 | Sircar |
| 5,204,075 A | 4/1993 | Jain et al. |
| 5,270,000 A | 12/1993 | Goldner et al. |
| 5,283,035 A | 2/1994 | Karthaus et al. |
| 5,290,345 A | 3/1994 | Osendorf et al. |
| 5,511,409 A | 4/1996 | Knaebel |
| 5,522,808 A | 6/1996 | Skalla |
| 5,607,652 A | 3/1997 | Hellmuth et al. |
| 5,641,455 A | 6/1997 | Rosenlund et al. |
| 5,702,669 A | 12/1997 | Green |
| 5,741,470 A | 4/1998 | Wenzler |
| 5,755,857 A | 5/1998 | Acharya et al. |
| 5,779,773 A | 7/1998 | Cam et al. |
| 5,883,199 A | 3/1999 | McCarthy et al. |
| 5,964,927 A | 10/1999 | Graham et al. |
| 6,156,101 A | 12/2000 | Naheiri |
| 6,684,648 B2 | 2/2004 | Faqih |
| 6,743,402 B2 | 6/2004 | Shimakawa |
| 7,625,535 B2 | 12/2009 | Yamaguchi |
| 8,110,156 B2 | 2/2012 | Ricciardi et al. |
| 8,431,085 B2 | 4/2013 | Froderberg et al. |
| 9,616,143 B2 | 4/2017 | Snyder et al. |
| 10,987,443 B1 | 4/2021 | Hu et al. |
| 2001/0033838 A1 | 10/2001 | Farmer |
| 2002/0046569 A1 | 4/2002 | Faqih |
| 2002/0197194 A1 | 12/2002 | Machado et al. |
| 2004/0229340 A1 | 11/2004 | Kawai |
| 2006/0236860 A1 | 10/2006 | Sumida et al. |
| 2006/0249027 A1 | 11/2006 | Adolphsen et al. |
| 2007/0209383 A1 | 9/2007 | Hutton |
| 2008/0078289 A1 | 4/2008 | Sergi et al. |
| 2008/0080999 A1 | 4/2008 | Bondar |
| 2008/0289591 A1 | 11/2008 | Tessier et al. |
| 2010/0196194 A1 | 8/2010 | Voeten et al. |
| 2010/0291169 A1 | 11/2010 | Toreki et al. |
| 2011/0265644 A1 | 11/2011 | Swami et al. |
| 2012/0031268 A1 | 2/2012 | Yaghi et al. |
| 2012/0298207 A1 | 11/2012 | Woelk et al. |
| 2014/0119989 A1 | 5/2014 | Hayashi |
| 2014/0251130 A1 | 9/2014 | Sprinkle et al. |
| 2014/0290162 A1 | 10/2014 | Tanimoto |
| 2016/0010883 A1 | 1/2016 | Jornitz et al. |
| 2016/0130489 A1 | 5/2016 | Gilmour |
| 2017/0056813 A1 | 3/2017 | McMahon et al. |
| 2019/0076776 A1 | 3/2019 | Mahecha-Botero et al. |
| 2019/0151791 A1 | 5/2019 | Awadh et al. |
| 2019/0175971 A1 | 6/2019 | Moore et al. |
| 2020/0148655 A1 | 5/2020 | Duff et al. |

FOREIGN PATENT DOCUMENTS

| | | |
|---|---|---|
| CN | 101224381 A | 7/2008 |
| CN | 101549241 A | 10/2009 |
| CN | 101773762 A | 7/2010 |
| CN | 201632182 U | 11/2010 |
| CN | 102173384 A | 9/2011 |
| CN | 102219642 A | 10/2011 |
| CN | 102302791 A | 1/2012 |
| CN | 102921570 A | 2/2013 |
| CN | 202802975 U | 3/2013 |
| CN | 202933710 U | 5/2013 |
| CN | 203183363 U | 9/2013 |
| CN | 103386141 A | 11/2013 |
| CN | 103394109 A | 11/2013 |
| CN | 103394278 A | 11/2013 |
| CN | 103657383 A | 3/2014 |
| CN | 103667014 A | 3/2014 |
| CN | 103706233 A | 4/2014 |
| CN | 203507806 U | 4/2014 |
| CN | 203564952 U | 4/2014 |
| CN | 103800926 A | 5/2014 |
| CN | 103801190 A | 5/2014 |
| CN | 103908688 A | 7/2014 |
| CN | 203749877 U | 8/2014 |
| CN | 203750388 U | 8/2014 |
| CN | 203750389 U | 8/2014 |
| CN | 104014227 A | 9/2014 |
| CN | 104275085 A | 1/2015 |
| CN | 104307008 A | 1/2015 |
| CN | 204261680 U | 4/2015 |
| CN | 204447972 U | 7/2015 |
| CN | 104815535 A | 8/2015 |
| CN | 104946557 A | 9/2015 |
| CN | 105132060 A | 12/2015 |
| CN | 105327665 A | 2/2016 |
| CN | 105664822 A | 2/2016 |
| CN | 105462903 A | 4/2016 |
| CN | 205300112 U | 6/2016 |
| CN | 210721130 U | 6/2016 |
| CN | 106139199 A | 11/2016 |
| CN | 106421844 A | 2/2017 |
| CN | 106475021 A | 3/2017 |
| CN | 106582126 A | 4/2017 |
| CN | 106754585 | 5/2017 |
| CN | 107058179 A | 8/2017 |
| CN | 206443946 U | 8/2017 |
| CN | 206535551 U | 10/2017 |
| CN | 107460146 A | 12/2017 |
| CN | 206853397 U | 1/2018 |
| CN | 107677016 A | 2/2018 |
| CN | 207169397 U | 4/2018 |
| CN | 207187436 U | 4/2018 |
| CN | 107988095 A | 5/2018 |
| CN | 207356290 U | 5/2018 |
| CN | 207745676 U | 8/2018 |
| CN | 207913454 U | 9/2018 |
| CN | 108607511 A | 10/2018 |
| CN | 208047841 U | 11/2018 |
| CN | 208218734 U | 12/2018 |
| CN | 109294942 A | 2/2019 |
| CN | 109382064 A | 2/2019 |
| CN | 208448985 U | 2/2019 |

(56) References Cited

FOREIGN PATENT DOCUMENTS

| | | |
|---|---|---|
| CN | 208893903 U | 5/2019 |
| CN | 110106086 A | 8/2019 |
| CN | 110145747 A | 8/2019 |
| CN | 110302634 A | 10/2019 |
| CN | 110404485 A | 11/2019 |
| CN | 110461371 A | 11/2019 |
| CN | 209662917 U | 11/2019 |
| CN | 110833754 A | 2/2020 |
| CN | 210021633 U | 2/2020 |
| CN | 210088451 U | 2/2020 |
| CN | 111117931 A | 5/2020 |
| CN | 111117932 A | 5/2020 |
| CN | 111154684 A | 5/2020 |
| CN | 111154687 A | 5/2020 |
| DE | 4236622 C1 | 3/1994 |
| EP | 0130319 A2 | 1/1985 |
| EP | 0350677 A1 | 1/1990 |
| EP | 1238718 A1 | 9/2002 |
| GB | 1472091 A | 4/1977 |
| JP | 2008114210 A | 5/2008 |
| JP | 2013172790 A | 10/2016 |
| JP | 2016221497 A | 12/2016 |
| JP | 2010259648 A | 5/2018 |
| WO | 1302478 A1 | 4/2003 |
| WO | WO 2006115199 A1 | 11/2006 |
| WO | WO2011002277 A1 | 1/2011 |
| WO | WO 2012013197 A2 | 2/2012 |
| WO | 2883598 A1 | 6/2015 |
| WO | WO-2019-136504 A1 | 7/2019 |
| WO | WO 2019236249 A1 | 12/2019 |

OTHER PUBLICATIONS

Brown, et al., (1997) J. Ag and Food Chem. 3(45): 955-961, "Degradation of Thifensulfuron Methyl in Soil: Role of Microbial Carboxyesterase Activity".

Danko, et al., (2008) Proc. Biochem. 43:517-521, "Involvement of carbon dioxide in the aerobic biodegradation of ethylene oxide, ethene, and vinyl chloride".

Derwent-Acc-No. 2017-83105H (2017) "New Bacillus coagulans i.e. Bacillus coagulans Daoduo 4 and method (M1) for screening the B. coagulans". Abstract only, 1 pg.

Fei, et al. (2006) Annals Micro. 3(56):201-205, "Identification of *Enterococcus* sp. from midgut of silkworm based on biochemical and 16S rDNA sequencing analysis".

International Search Report and Written Opinion dated Oct. 28, 2020 in PCT/CN2020/101143, 10 pages.

International Search Report and Written Opinion dated Oct. 21, 2020 in PCT/CN2020/101141, 12 pages.

International Search Report and Written Opinion dated Oct. 27, 2020 in PCT/CN2020/101138, 11 pages.

International Search Report and Written Opinion dated Oct. 28, 2020 in PCT/CN2020/101144, 10 pages.

International Search Report and Written Opinion dated Oct. 28, 2020 in PCT/CN2020/101139, 11 pages.

Khatiwala, et al. (2008) J. Polym. Environ. 16:61-67, "Biodegradation of poly(ε-caprolactone)(PCL) film by alcaligenes faecalis".

Liao, et al., (2001) Environ. Tech. 22:165-173, "Decomposition of ethylene oxide in the RF plasma environment".

Perez-Cano, et al., (2010) Immunobiology 215:996-1004, "In viro immunomodulatory activity of Lactobacillus fermentum CECT5716 and Lactobacillus salivarius CECT5713: two probiotic strains isolated from human breast milk".

Poelarends, et al., (1999) J. Bact. 7(181):2050-2058, "Degradation of 1, 2-Dibromoethane by *Mycobacterium* sp. Strain GP1".

Shin, et al., (2016) Anaerobe 39:14-18, "*Clostridium kogasensis* sp. nov., a novel member of the genus *Clostridium*, isoloated from soil under a corroded gas pipeline".

Sutton, et al. (2018) F1000 Research 7:1-26, "*Enterobacter hormaechei* subsp. *hoffmannii* subsp. nov., *Enterobacter hormaechei* subsp. *xiangfangensis* comb, nov., *Enterobacter roggenkampii* sp. nov., and *Enterobacter muelleri* is a later heterotypic synonym of *Enterobacter asburiae* based on computational analysis of sequenced *Enterobacter* genomes".

Taylor, et al., (2010) Appl. Micro. Biotech. 87:2293-2302, "Extending the alkene substrate range of vinyl chloride utilizing *Nocardioides* sp. strain JS614 with ethene oxide".

International Search Report and Written Opinion dated Dec. 16, 2020 in PCT/CN2020/101142, 11 pages.

International Search Report & Written Opinion for PCT/CN2020/100113 as prepared by the Chinese International Searching Authority dated Mar. 31, 2021, 10 pages.

International Search Report & Written Opinion for PCT/CN2020/100122 as prepared by the Chinese International Searching Authority dated Mar. 26, 2021, 11 pages.

International Search Report & Written Opinion for PCT/CN2020/100120 as prepared by the Chinese International Searching Authority dated Mar. 31, 2021, 10 pages.

International Search Report and Written Opinion, in PCT/CN2020/101140 dated Dec. 21, 2020, 11 pages.

International Search Report and Written Opinion, in PCT/CN2020/100143 dated Dec. 21, 2020, 9 pages.

International Search Report and Written Opinion, in PCT/CN2020/100125 dated Dec. 23, 2020, 9 pages.

International Search Report and Written Opinion, in. PCT/CN2020/100115 dated Dec. 16, 2020, 11 pages.

International Search Report and Written Opinion, in. PCT/CN2020/100119 dated Dec. 17, 2020, 9 pages.

International Search Report and Written Opinion, in PCT/CN2020/100144 dated Dec. 18, 2020, 10 pages.

Kahm et al., 2018 "Lyapunov exponents with Model Predictive Control for exothermic batch reactors" IFAC-PapersOnline, 51, 417-422.

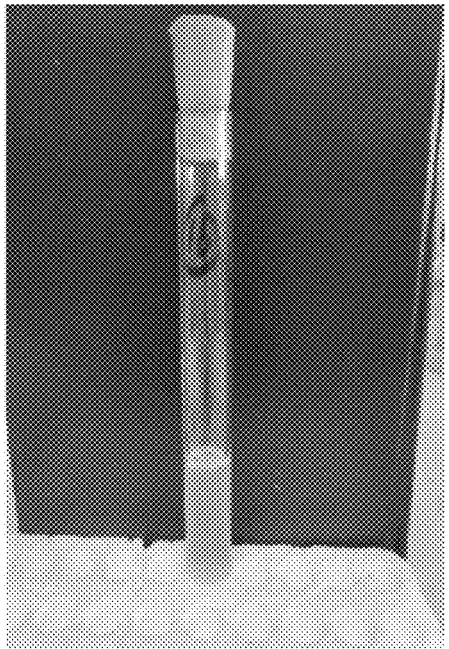
FIG. 4A FIG. 4B
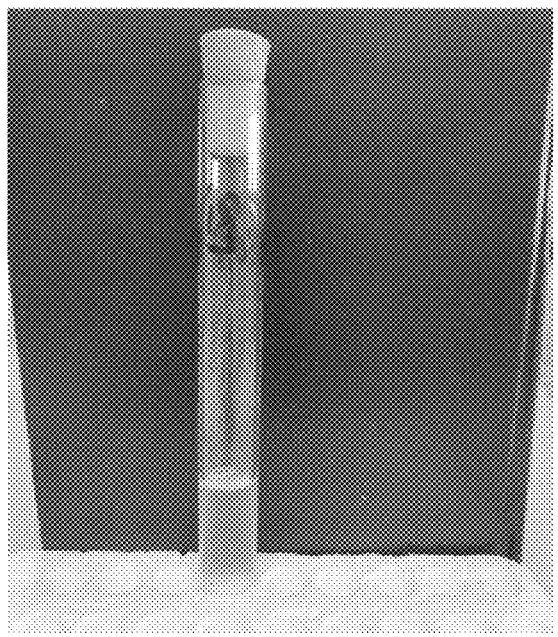
FIG. 5A FIG. 5B

 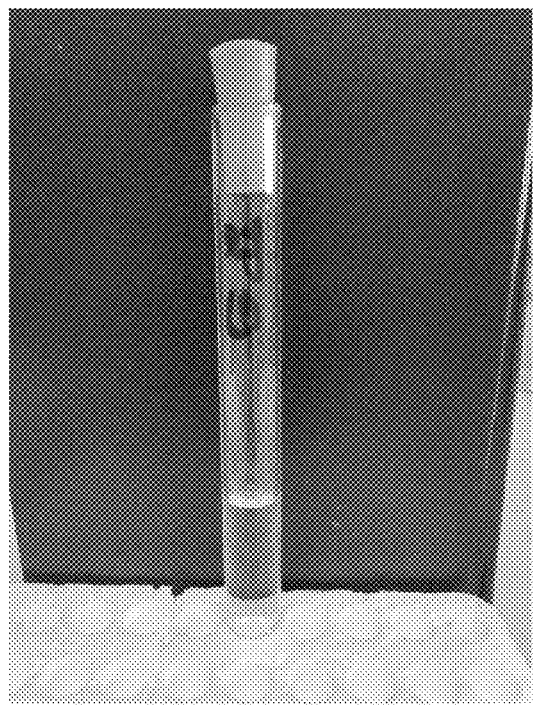
FIG. 6A                    FIG. 6B

BACTERIA FOR DEGRADING ETHYLENE OXIDE AND APPLICATIONS THEREOF

CROSS-REFERENCE TO RELATED PATENT APPLICATIONS

This application is a Bypass Continuation of PCT/CN2020/101138, filed Jul. 9, 2020, which application claims the benefit of Chinese Patent Application No. 202010064774.6, filed on Jan. 20, 2020, Chinese Patent Application No. 202010062774.2, filed on Jan. 20, 2020, Chinese Patent Application No. 202010062877.9, filed on Jan. 20, 2020 and Chinese Patent Application No. 202010064633.4, filed on Jan. 20, 2020, the entire contents of which are incorporated herein by reference in their entirety for all purposes.

TECHNICAL FIELD

The present disclosure relates to the field of microbial technology, and more particularly to several bacterial strains capable of degrading ethylene oxide and uses thereof.

SEQUENCE STATEMENT

Incorporated by reference herein in its entirety is the Sequence Listing entitled "1211_CK03_ST25_PCT" created Jun. 1, 2020, size of 6.52 kilobytes.

BACKGROUND

Ethylene oxide (EO) is one of the important petrochemical products in modern engineering. It is a broad-spectrum and highly effective sterilization agent and disinfectant. Ethylene oxide can kill most bacteria, spores, viruses and fungi and has a strong penetrating power to reach depth of an article, therefore playing an irreplaceable role in medical sterilization and related industries. However, ethylene oxide is extremely active, flammable and explosive, and is also recognized as a carcinogen globally, which set barriers to the application of ethylene oxide.

At present, there are two main methods for industrial disposal of ethylene oxide in waste gas and waste water. One way is neutralization of ethylene oxide by use of sulfuric acid, but it has relatively low absorption saturability and treatment efficiency, while producing undesirable by-products, increasing disposal costs. Another method is oxidation of ethylene oxide by use of an oxidation reaction furnace, which requires very strict control of technical parameters and is subject to high risks of explosion.

Therefore, there is an urgent and long-felt need to find a safe and effective way of disposal of ethylene oxide in waste gas and waste water. Microbial degradation of harmful substances plays an important role in the chemical industry. However, there are few studies on the use of microorganisms to degrade ethylene oxide and no reports of bacteria or their uses on effective degradation of ethylene oxide.

SUMMARY

In view of the above, the present disclosure provides a variety of bacteria strains that can effectively degrade ethylene oxide, which can be used to degrade ethylene oxide pollutants, greatly improve the decontamination disposal capacity of ethylene oxide, and reduce the environmental risks related to ethylene oxide pollution such as risk in public health.

In one aspect of the present disclosure, it provides a *Kurthia gibsonii* strain EO-06 with Deposit Number of CGMCC No. 18436.

In one aspect of the present disclosure, it provides a *Clostridium kogasensis* strain EO-08 with Deposit Number of CGMCC No. 18438.

In one aspect of the present disclosure, it provides a *Clostridium acidisoli* strain EO-09 with Deposit Number of CGMCC No. 18439.

In one of the aspects of the present disclosure, there is provided a strain capable of degrading ethylene oxide, which is: a *Kurthia gibsonii* strain comprising the 16S rDNA sequence of SEQ ID NO: 3; a *Clostridium kogasensis* strain comprising the 16S rDNA sequence of SEQ ID NO: 4; or a *Clostridium acidisoli* strain comprising the 16S rDNA sequence of SEQ ID NO: 5. These strains can effectively degrade ethylene oxide.

In another aspect of the present disclosure, it provides a degradation agent for degrading ethylene oxide, comprising one or more strains selected from the group consisting of: a *Kurthia gibsonii* strain EO-06 with Deposit Number of CGMCC No. 18436; a *Clostridium kogasensis* strain EO-08 with Deposit Number of CGMCC No. 18438; a *Clostridium acidisoli* strain EO-09 with Deposit Number of CGMCC No. 18439, a *Kurthia gibsonii* strain comprising the 16S rDNA sequence of SEQ ID NO: 3; a *Clostridium kogasensis* strain comprising the 16S rDNA sequence of SEQ ID NO: 4; or a *Clostridium acidisoli* strain comprising the 16S rDNA sequence of SEQ ID NO: 5.

In some of the embodiments, the degradation agent is prepared by culturing the corresponding strain or combination of strains.

In some of the embodiments, a final concentration of the corresponding strain or combination of strains in the degradation agent is at least $10^8$ cfu/mL, or from $10^8$ cfu/mL to $10^{10}$ cfu/mL.

In another aspect of the present disclosure, it provides a method for preparing a degradation agent for degrading ethylene oxide, comprising: incubating one or more strains selected from the group consisting of the following strains in a liquid Sabouraud medium and at a temperature of 20-40° C.: a *Kurthia gibsonii* strain EO-06 with Deposit Number of CGMCC No. 18436; a *Clostridium kogasensis* strain EO-08 with Deposit Number of CGMCC No. 18438; a *Clostridium acidisoli* strain EO-09 with Deposit Number of CGMCC No. 18439; a *Kurthia gibsonii* strain comprising the 16S rDNA sequence of SEQ ID NO: 3; a *Clostridium kogasensis* strain comprising the 16S rDNA sequence of SEQ ID NO: 4; or a *Clostridium acidisoli* strain comprising the 16S rDNA sequence of SEQ ID NO: 5.

In some of the embodiments, the liquid Sabouraud medium comprises, by mass, 40 parts of glucose, and 10 parts peptone, which are brought to 1000 parts with water in volume and adjusted to a pH of 5.4-5.8.

In another aspect of the present disclosure, it provides a method for manufacturing bacteria for degrading ethylene oxide, comprising: incubating one or more strains selected from the group consisting of the following strains in a liquid Sabouraud medium and at a temperature of 20-40° C.: a *Kurthia gibsonii* strain EO-06 with Deposit Number of CGMCC No. 18436; a *Clostridium kogasensis* strain EO-08 with Deposit Number of CGMCC No. 18438; a *Clostridium acidisoli* strain EO-09 with Deposit Number of CGMCC No. 18439; a *Kurthia gibsonii* strain comprising the 16S rDNA sequence of SEQ ID NO: 3; a *Clostridium kogasensis* strain comprising the 16S rDNA sequence of SEQ ID NO:

4; or a *Clostridium acidisoli* strain comprising the 16S rDNA sequence of SEQ ID NO: 5.

In some of the embodiments, the liquid Sabouraud medium comprises: by mass, 40 parts of glucose, and 10 parts of peptone, which are brought to 1000 parts with water in volume and adjusted to a pH of 5.4-5.8.

In one of the aspects of the present disclosure, it provides a method, for decreasing the amount of ethylene oxide in sample, comprising adding to a sample comprising ethylene oxide an amount a pure culture of an *Kurthia gibsonii*; *Clostridium kogasensis*, or *Clostridium acidisoli* strain bacterium, allowing the bacterium to degrade the ethylene oxide, thereby decreasing the amount of ethylene oxide, wherein the 16S rDNA sequence of the *Kurthia gibsonii* strain bacterium is SEQ ID NO: 3; the 16S rDNA sequence of the *Clostridium kogasensis* strain bacterium is SEQ ID NO: 4; or the 16S rDNA sequence of the *Clostridium acidisoli* strain bacterium is SEQ ID NO: 5.

In a further aspect of the method, the *Kurthia gibsonii*, *Clostridium kogasensis*, or *Clostridium acidisoli* strain bacterium is capable of using ethylene oxide as a carbon source and is capable of growing normally with ethylene oxide as the sole carbon source in the culture.

In a further aspect of the method, the *Kurthia gibsonii* strain bacterium is *Kurthia gibsonii* strain EO-06 with Deposit Number of CGMCC No. 18436; the *Clostridium kogasensis* strain is *Clostridium kogasensis* strain EO-08 with Deposit Number of CGMCC No. 18438; and the *Clostridium acidisoli* strain is *Clostridium acidisoli* strain EO-09 with Deposit Number of CGMCC No. 18439.

In another aspect of the present disclosure, it provides a method for biodegrading ethylene oxide, comprising: degrading ethylene oxide with one or more strains one or more strains selected from the group consisting of a *Kurthia gibsonii* strain EO-06 with Deposit Number of CGMCC No. 18436, a *Clostridium kogasensis* strain EO-08 with Deposit Number of CGMCC No. 18438; a *Clostridium acidisoli* strain EO-09 with Deposit Number of CGMCC No. 18439; a *Kurthia gibsonii* strain comprising the 16S rDNA sequence of SEQ ID NO: 3; a *Clostridium kogasensis* strain comprising the 16S rDNA sequence of SEQ ID NO: 4; and a *Clostridium acidisoli* strain comprising the 16S rDNA sequence of SEQ ID NO: 5, or the aforementioned degradation agent, or the degradation agent prepared according to the aforementioned method.

In some of the embodiments, the method above is used to degrade ethylene oxide in waste gas or waste water and comprises mixing the waste gas or waste water with one or more strains selected from the group consisting of a *Kurthia gibsonii* strain EO-06 with Deposit Number of CGMCC No. 18436, a *Clostridium kogasensis* strain EO-08 with Deposit Number of CGMCC No. 18438; and a *Clostridium acidisoli* strain EO-09 with Deposit Number of CGMCC No. 18439, or the aforementioned degradation agent, or the degradation agent prepared according to the aforementioned method.

In some of the embodiments, the degrading ethylene oxide with one or more strains selected from the group consisting of a *Kurthia gibsonii* strain EO-06 with Deposit Number of CGMCC No. 18436, a *Clostridium kogasensis* strain EO-08 with Deposit Number of CGMCC No. 18438; a *Clostridium acidisoli* strain EO-09 with Deposit Number of CGMCC No. 18439; a *Kurthia gibsonii* strain comprising the 16S rDNA sequence of SEQ ID NO: 3; a *Clostridium kogasensis* strain comprising the 16S rDNA sequence of SEQ ID NO: 4; and a *Clostridium acidisoli* strain comprising the 16S rDNA sequence of SEQ ID NO: 5, comprises: incubating the strain or combination of strains in a liquid Sabouraud medium and at a temperature of 20-40° C.

In some embodiments, the method comprises incubating the strain in liquid Sabouraud medium to a concentration from $10^{10}$ cfu/mL to $10^{12}$ cfu/mL, to obtain an activation liquid for degrading ethylene oxide.

In one embodiment, the method comprises the concentration of the strain for degrading ethylene oxide ranges from $10^8$ cfu/mL to $10^{10}$ cfu/mL.

In some embodiments of the methods, the degradation rate is at least 10%, 15%, 20%, 25%, 30%, 35%, 40%, 50%, 60%, 70%, 75%, 80%, 90%, 95%, 100%, 125%, 150%, 200%, 250%, 300%, 350%, 400%, 450%, 500%, 550%, 600%, 650%, 700%, 750%, 800%, 850%, 900%, 1000%, 1100%, 1200%, 1300%, 1400%, or 1500% greater relative to the degradation rate of ethylene oxide in the absence of a strain of the invention.

In another aspect of the present disclosure, it provides use of one or more strains selected from the group consisting of a *Kurthia gibsonii* strain EO-06 with Deposit Number of CGMCC No. 18436, a *Clostridium kogasensis* strain EO-08 with Deposit Number of CGMCC No. 18438; a *Clostridium acidisoli* strain EO-09 with Deposit Number of CGMCC No. 18439; a *Kurthia gibsonii* strain comprising the 16S rDNA sequence of SEQ ID NO: 3; a *Clostridium kogasensis* strain comprising the 16S rDNA sequence of SEQ ID NO: 4; and a *Clostridium acidisoli* strain comprising the 16S rDNA sequence of SEQ ID NO: 5, or the aforementioned degradation agent, or the degradation agent prepared according to the aforementioned method.

In another aspect of the present disclosure, it provides use of one or more strains selected from the group consisting of a *Kurthia gibsonii* strain EO-06 with Deposit Number of CGMCC No. 18436, a *Clostridium kogasensis* strain EO-08 with Deposit Number of CGMCC No. 18438; and a *Clostridium acidisoli* strain EO-09 with Deposit Number of CGMCC No. 18439, a *Kurthia gibsonii* strain comprising the 16S rDNA sequence of SEQ ID NO: 3; a *Clostridium kogasensis* strain comprising the 16S rDNA sequence of SEQ ID NO: 4; and a *Clostridium acidisoli* strain comprising the 16S rDNA sequence of SEQ ID NO: 5, in preparation of a degradation agent for degrading ethylene oxide.

In another aspect of the present disclosure, it provides method of performing ethylene oxide tolerance and degradation acclimation to bacteria with ethylene oxide degradation potential to prepare bacteria strain having ethylene oxide tolerance and degradation ability, comprising:

inducted acclimation for ethylene oxide tolerance, comprising: successively passaging the bacteria with ethylene oxide degradation potential by steaking the same on a series of acclimation medium for ethylene oxide tolerance containing a gradient of increasing ethylene oxide concentrations from 100 to 800 mg/L; after each passaging, incubating at 20-40° C. for 24 to 48 hours, and selecting a single colony with a largest radius for next passaging; and finally selecting a single colony with a largest colony radius on an acclimation medium containing ethylene oxide of 500-800 mg/L to obtain a bacteria strain of ethylene oxide tolerance; and inducted acclimation for ethylene oxide degradation ability, comprising: successively passaging the bacteria strain of ethylene oxide tolerance by steaking the same on a series of acclimation medium for ethylene oxide degradation containing ethylene oxide of 500-800 mg/L and a gradient of decreasing proportion of carbon source from 50% to 0%; after each passaging, incubating at 20-40° C. for 24 to 48 hours, and selecting a single colony with a largest radius for next passaging; and finally selecting a single colony with a largest colony radius on the acclimation medium containing 500-800 mg/L of ethylene oxide and 0% of carbon source to obtain the bacteria strain having ethylene oxide tolerance and degradation ability.

In some of the embodiments, the series of acclimation medium for ethylene oxide tolerance have ethylene oxide concentrations increasing between 100 and 800 mg/L and comprises, by mass, 10 parts of peptone, 40 parts of glucose, and 15 parts of agar, which are mixed with water, adjusted to a pH of 5.4-5.8, and the volume brought to 1000 parts with water.

In some of the embodiments, the series of acclimation medium for ethylene oxide degradation have an ethylene oxide concentration of 500-800 mg/L and comprises, by mass, 10 parts of peptone, glucose decreasing from 20 parts to 0 parts, and agar 15 parts, which are mixed with water, adjusted to a pH of 5.4-5.8, and the volume brought to 1000 parts with water.

In another aspect of the present disclosure, it provides a method for screening and purifying bacteria with potential of ethylene oxide degradation, comprising: collecting microbial active sludge mixture containing ethylene oxide; mixing the sludge mixture with phosphate buffer, clarifying and filtering to obtain a suspension; incubating the suspension in an enriched medium containing ethylene oxide at a temperature of 20-40° C., to obtain a bacterial suspension capable of surviving an environment containing ethylene oxide; and incubating the bacterial suspension in a screening and purification medium containing ethylene oxide at a temperature of 20-40° C. to obtain the bacteria with potential of ethylene oxide degradation.

In some of the embodiments, the enriched medium containing ethylene oxide has an ethylene oxide concentration of 100 mg/L and comprises, by mass, 40 parts of glucose, and 10 parts of peptone, which are brought to 1000 parts with water in volume and adjusted to a pH of 5.4-5.8.

In some of the embodiments, the screening and purification medium containing ethylene oxide has an ethylene oxide concentration of 100 mg/L and comprises, by mass, 40 parts of glucose, and 10 parts peptone, which are brought to 1000 parts with water in volume and adjusted to a pH of 5.4-5.8.

This disclosure provides a variety of bacteria strains capable of degrading ethylene oxide and the applications thereof. It can be used to treat pollution, for example, to treat industrial or medical waste gas or waste-water containing ethylene oxide. The bacteria strains disclosed herein are easy to manufacture and can efficiently degrade high-concentration ethylene oxide in a short period of time without other carbon sources, which greatly improves the decontamination disposal capacity of ethylene oxide in industries.

The deposit information of the three strains for degrading ethylene oxide mentioned disclosed herewith is as follows:

The *Kurthia gibsonii* strain EO-06 with Deposit Number of CGMCC No. 18436, the *Clostridium kogasensis* strain EO-08 with Deposit Number of CGMCC No. 18438 and the *Clostridium acidisoli* strain EO-09 with Deposit Number of CGMCC No. 18439 were deposited on Aug. 29, 2019 at China General Microbiological Culture Collection Center (CGMCC) of China Committee for Culture Collection of Microorganisms with the deposit address being Institute of Microbiology of Chinese Academy of Sciences, NO. 1 West Beichen Road, Beijing 100101, China.

BRIEF DESCRIPTION OF DRAWINGS

FIGS. 4A-4B show bacterial colony growth of *Kurthia gibsonii* EO-06 strain, which was originally obtained by enrichment, purification and screening processes according to Example 1 of the present disclosure, after the inducted acclimation of Example 2 (FIG. 4A), and before the inducted acclimation (FIG. 4B) of Example 2 in a liquid medium with 800 mg/L ethylene oxide after growing at a constant temperature of 37° C. for 48 hours in the comparative ethylene oxide degradation test according to Example 3.

FIGS. 5A-5B show bacterial colony growth of *Clostridium kogasensis* EO-08 strain, which was originally obtained by enrichment, purification and screening processes according to Example 1 of the present disclosure, after the inducted acclimation of Example 2 (FIG. 5A) and (FIG. 5B) before the inducted acclimation of Example 2 in a liquid medium with 800 mg/L ethylene oxide after growing at a constant temperature of 37° C. for 48 hours in the comparative ethylene oxide degradation test according to Example 3.

FIGS. 6A-6B show bacterial colony growth of *Clostridium acidisoli* EO-09 strain, which was originally obtained by enrichment, purification and screening processes according to Example 1 of the present disclosure, after the inducted acclimation of Example 2 (FIG. 6A) and (FIG. 6B) before the inducted acclimation of Example 2 in a liquid medium with 800 mg/L ethylene oxide after growing at a constant temperature of 37° C. for 48 hours in the comparative ethylene oxide degradation test according to Example 3.

DETAILED DESCRIPTION OF EMBODIMENTS

Figure 1A:
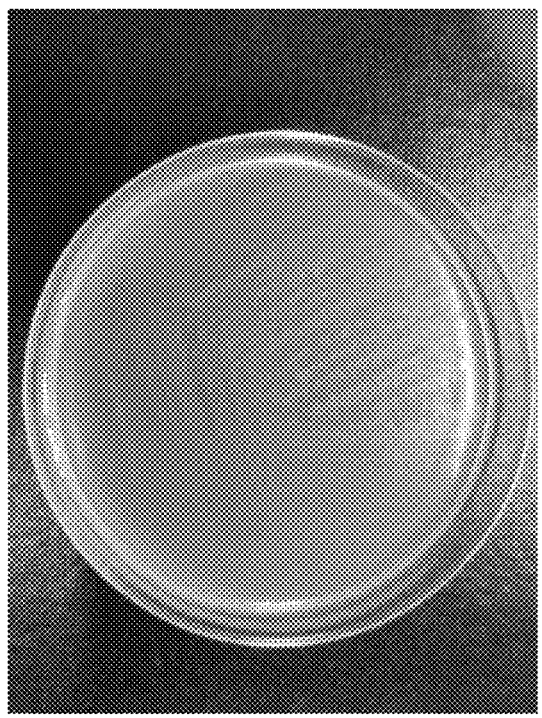
FIGS. 1A-1C show bacterial colony growth of the EO-degrading potential bacteria in the enrichment medium B after growing for 48 hours at a constant temperature of 37° C., wherein the EO-degrading potential bacteria were FIG. 1A, *Kurthia gibsonii* EO-06 original strain, FIG. 1B, *Clostridium kogasensis* EO-08 original strain and FIG. 1C *Clostridium acidisoli* EO-09 original strain obtained by the enrichment, purification and screening processes according to Example 1 of the present disclosure.

Detailed description will be given below with referral to the accompanying figures to facilitate understanding of the present application. Preferred examples are shown in the figures. However, the present application may be implemented in various ways, without being limited to the examples presented in the description. The purpose of these embodiments is merely for illustration and better comprehension of the present disclosure.

Unless otherwise defined, all the technical and scientific terms herein shall be understood as the same meaning with those commonly accepted by a person skilled in the art. Such terms, as used herein, are for the purpose of describing specific embodiments of, without limiting, the present application. The term "and/or" as used herein refers to any and all combinations of one or more items recited.

The present disclosure also provides methods for screening and purifying bacteria capable of degrading of ethylene oxide, comprising: collecting sludge containing ethylene oxide and with microbial activity, for example, collecting sewage or sludge samples from a sewage outlet of a sewage treatment plant or chemical plant; allowing tolerance enrichment culture of the samples in enrichment medium containing ethylene oxide (for example, 100 mg/L) to obtain a suspension of bacteria that can survive in an environment containing ethylene oxide; and, inoculating the suspension of bacteria to screening and purification medium containing ethylene oxide (for example, 100 mg/L) for screening and purification of original strains with potential for degrading ethylene oxide.

The present disclosure also provides methods for inducted acclimation of bacteria toward EO degradation, comprising:

method for acclimation toward EO tolerance: successively passaging the original strains with the potential for ethylene oxide degradation by steaking on a series of plates of acclimation medium for ethylene oxide tolerance containing a gradient of increasing ethylene oxide concentrations; after each passaging, incubating under 20-40° C. for 24 to 48 hours, and selecting a single colony with the largest radius for the next passaging; and finally selecting a single colony with the largest colony radius on the acclimation medium plate containing the highest concentration of ethylene oxide to obtain a predominant strain of ethylene oxide degradation; and method for acclimation toward EO degradation: successively passaging the predominant strain of ethylene oxide degradation by steaking on a series of plates of acclimation medium for ethylene oxide degradation containing a high concentration of ethylene oxide and a gradient of decreasing proportion of carbon source; after each passaging, incubating under 20-40° C. for 24 to 48 hours, and selecting a single colony with the largest radius for the next passaging; and finally selecting a single colony with the largest colony radius on the acclimation medium plate containing the high concentration of ethylene oxide and 0% of carbon source to obtain a predominant strain of ethylene oxide tolerance and degradation.

The chemicals in the following specific examples of the present disclosure were all commercially available, and the methods not described are conventional experimental methods, which will not be elaborated here.

Enrichment, Purification, Screening and Identification of Strains with Ethylene Oxide Degradation Ability Below is an exemplary example of enrichment, purification, screening, and identification of strains with ethylene oxide degradation ability.

EXAMPLE 1

I. Enrichment, Purification and Screening

A sample of the sludge mixture was collected at the sewage outlet of a suburban sewage treatment plant in Guangzhou, Guangdong Province, and used for purpose of this example.

Enrichment medium A was prepared as the following: 40 g of glucose, and 10 g of peptone were brought to 1000 mL with water in volume and adjusted to pH 5.4-5.8, and the volume adjusted to 1000 mL with distilled water. Portions of 250 ml of the prepared medium were added to 500 mL Erlenmeyer flasks, sterilized at 121° C. for 20 min, and cooled to room temperature. Pure ethylene oxide liquid was placed on an ice box before 28 µL was taken and injected into the sterilized medium by a sealed syringe, providing 100 mg/L of ethylene oxide in the medium complying with the national emission standard, to obtain the enrichment medium A.

The screening and purification medium was prepared as follows: 40 g of glucose, 10 g of peptone, and 15 g of agar were brought to 1000 mL with water in volume and adjusted to pH 5.4-5.8, and the volume brought to 1000 mL with distilled water. Portions of 250 ml of the prepared selection medium were added into 500 mL Erlenmeyer flasks, sterilized at 121° C. for 20 minutes, and cooled to about 50-56° C. 28 µL (or 25 mg) of ethylene oxide liquid was injected into the sterilized medium by a sealed syringe to obtain the screening and purification medium.

Enrichment medium B was prepared as the following: 40 g of glucose, 10 g of peptone were brought to 1000 mL with water in volume and adjusted to pH 5.4-5.8. Portions of 250 ml of the prepared medium were added to 500 mL Erlenmeyer flasks, sterilized at 121° C. for 20 min, and cooled to room temperature to obtain the enrichment medium B.

10.0 g of the sludge mixture sample was weighed, added with 100 mL of 0.03 mol/L phosphate buffer, well mixed, allowed to stand for 120 min for clarification, and filtered to remove large particles of sediment and obtain a suspension. 1 mL of the suspension was added to 10 mL of liquid enrichment medium and placed in a shaker for oxygen-consuming enrichment culture for 24-48 h (200 rpm, 37° C.) and the growth status was observed.

The predominant strains from the enrichment medium A were streaked on the screening and purification medium for separation to obtain predominant strains for ethylene oxide degradation.

The predominant strains for ethylene oxide degradation were selected and cultured in the enrichment medium B for 24 hours to obtain three EO-degrading potential strains, designated as the EO-06 original strain, the EO-08 original strain and the EO-09 original strain. The EO-degrading potential strains were preserved at −80° C. using the glycerin preservation method (culture medium:50% glycerol=1:1).

At 48 hours of culture in the screening and purification medium, the colony morphology of the original strain EO-06 was milky white, with irregular edges, radial shape, diameter 1.5-3.0 mm, and golden yellow pigment; the colony morphology of the original strain EO-08 was milky yellow, opaque or translucent, with uneven edges, diameter 2.0-2.5 mm, and no pigment; and the colony morphology of the original strain EO-09 was gray-white, opaque or translucent, with meteor-like loose colonies, irregular edges, and no pigment.

II. Characterization and Identification of EO-Degrading Bacteria Strains:

The following identification methods were used:

Morphological characterization: including observation of colony morphology, microscopic morphology, culture characteristics and Gram staining;

Physiological and biochemical characterization: including nutrition type, nitrogen and carbon source utilization capacity, and biochemical tests;

Molecular biological characterization (16s rDNA sequencing; (the DNA in the genome that produces the ribosomal RNA is called the "rRNA gene" or simply "rDNA"): including the procedure of bacterial culture, bacterial DNA extraction, PCR amplification, 16s rDNA sequencing and sequence alignment analysis, wherein the primer pair for PCR amplification was as follows:

Upstream primer 27F: 5'-AGAGTTT-GATCCTGGCTCAG-3', as shown in SEQ ID NO: 1; and

Downstream primer 1492R: 5'-GGTTACCTTGT-TACGACTT-3', as shown in SEQ ID NO: 2.

The above characterization and identification methods are well known to those skilled in the art.

Figure 1B:
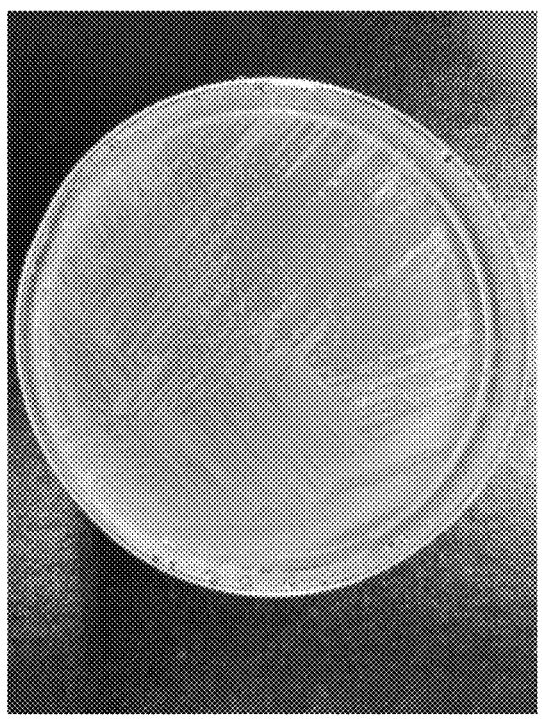
Figure 1C:
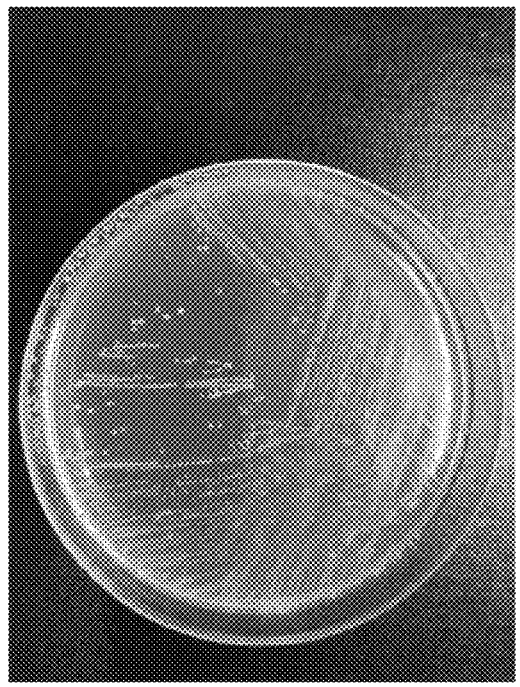
Figure 2A:
FIGS. 2A-2C show the Gram staining result of the EO-degrading potential bacteria, wherein the EO-degrading potential bacteria were, FIG. 2A, *Kurthia gibsonii* EO-06 original strain, FIG. 2B *Clostridium kogasensis* EO-08 original strain and FIG. 2C *Clostridium acidisoli* EO-09 original strain obtained by the enrichment, purification and screening processes according to Example 1 of the present disclosure.
Figure 2B:
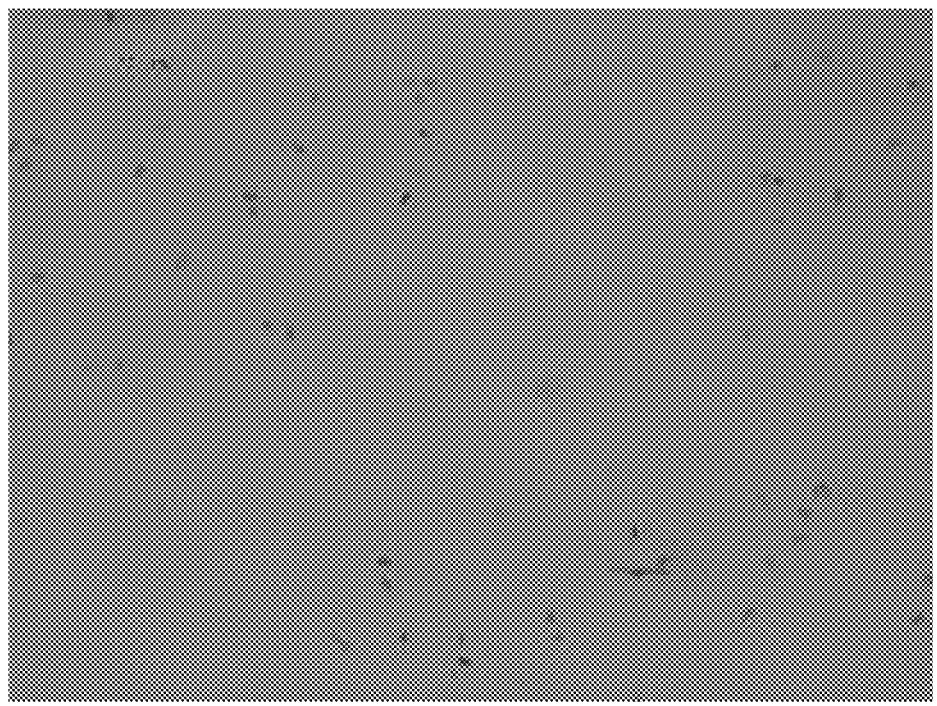
Figure 2C:
Figure 3A:
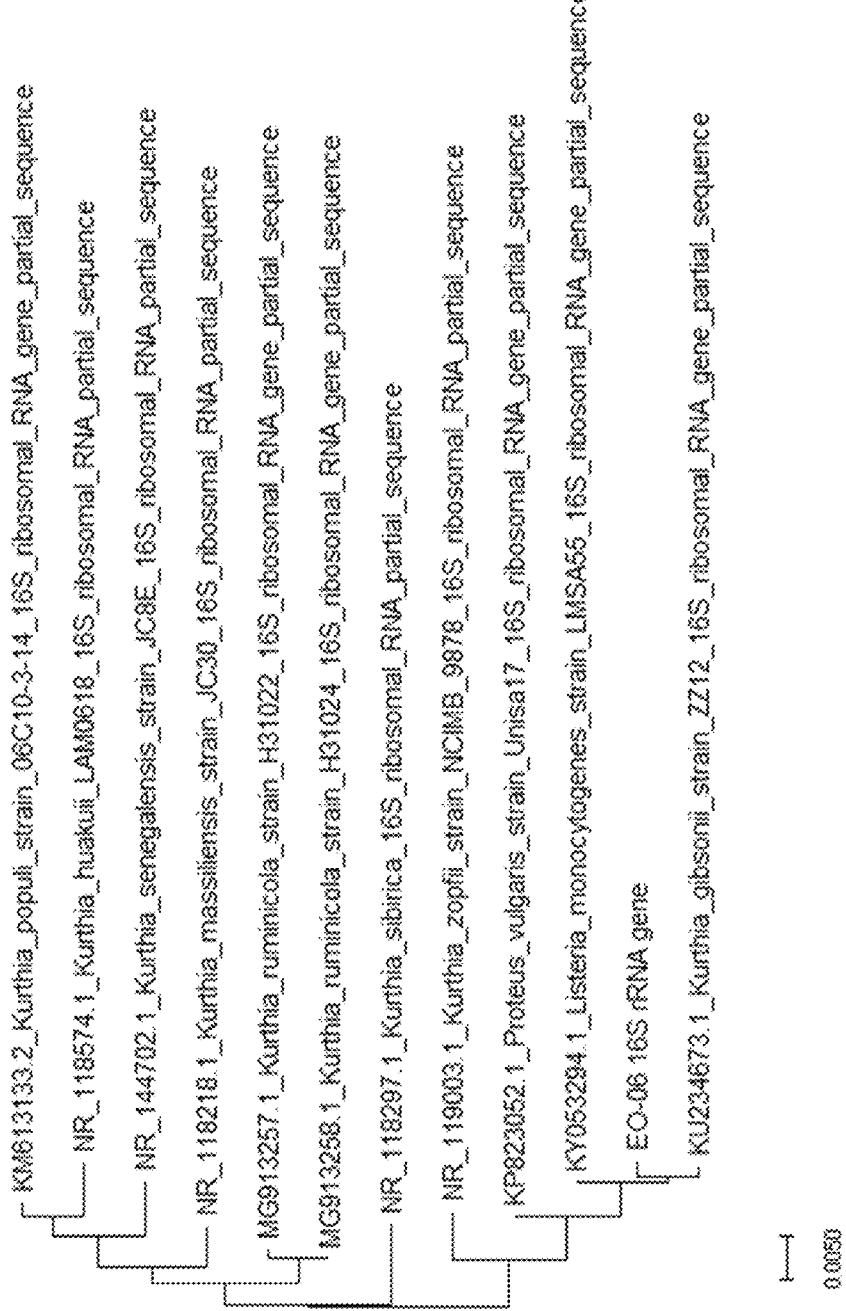
FIGS. 3A-3C show the phylogenetic evolution diagram of the EO-degrading potential bacteria, wherein the EO-degrading potential bacteria were (FIG. 3A) *Kurthia gibsonii* EO-06 original strain, (FIG. 3B) *Clostridium kogasensis* EO-08 original strain and (FIG. 3C) *Clostridium acidisoli* EO-09 original strain obtained by the enrichment, purification and screening processes according to Example 1 of the present disclosure.
Figure 3B:
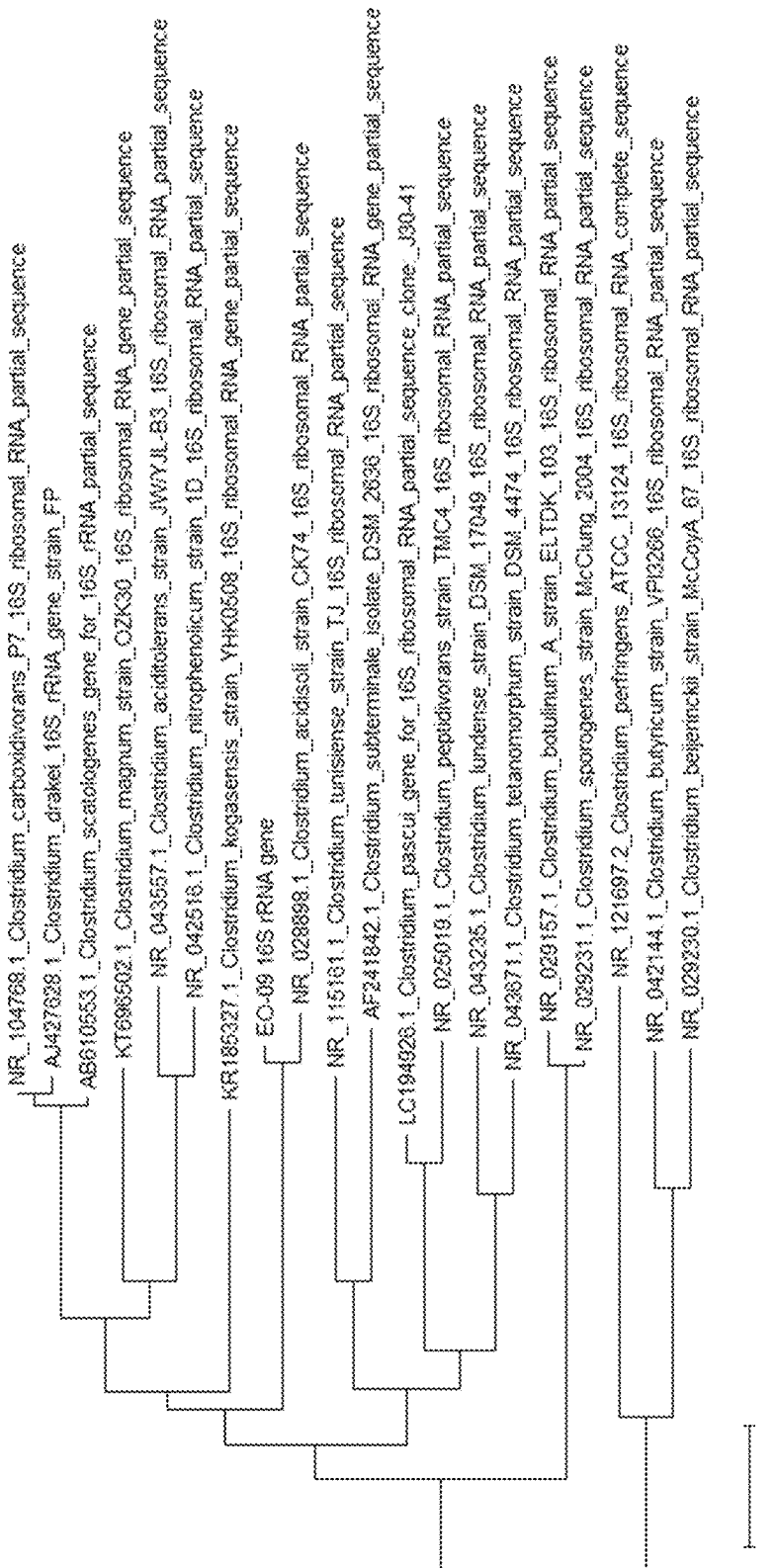
Figure 3C:
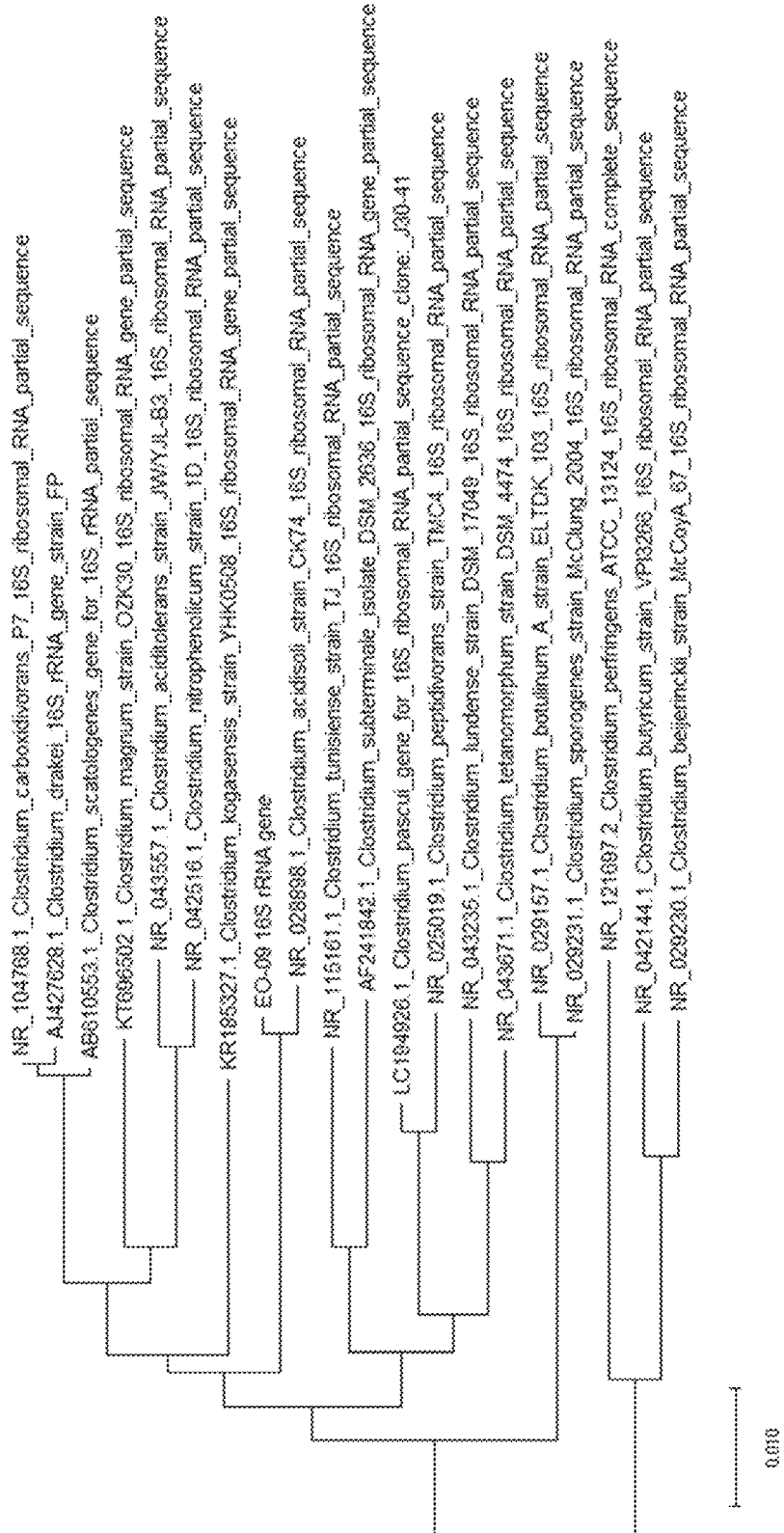

The colony morphologies of the original strain EO-06, the original strain EO-08, and the original strain EO-09 are shown in FIGS. 1A-1C, their Gram staining results shown in FIGS. 2A-2C, and their phylogenetic trees shown in FIGS. 3A-3C, respectively. According to the characterization results of morphology, physiology, biochemistry, and molecular biology, the original strain EO-06, the original strain EO-08 and the original strain EO-09 were *Kurthia gibsonii*, *Clostridium kogasensis* and *Clostridium acidisoli*, respectively. The characterization and identification results of the three EO-degrading potential strains are summarized in Table 1 below.

TABLE 1

Characterization and identification results of EO-06 original strain, EO-08 original strain, EO-09 original strain.

| Strain | EO-06 original strain | EO-08 original strain | EO-09 original strain |
|---|---|---|---|
| Colony Morphology | Milky white, with irregular edges, radial shape, diameter 1.5-3.0 mm, and golden yellow pigment. | Milky yellow, opaque or translucent, with uneven edges, diameter 2.0-2.5 mm, and no pigment. | Gray-white, opaque or translucent, with meteor-like loose colonies, irregular edges, and no pigment. |
| Microscopic morphology | Oval shape, no sporing. | Sporing with round or oval spores. | Rod-shaped, sporing. |
| Culture characteristics | Facultative anaerobic bacteria, sensitive to acid, suitable growth at temperature 20-35° C. | Anaerobic, good resistance to unfavorable environment. | Anaerobic. |
| Gram staining results | Gram-negative (red) | Gram-positive (purple) | Gram-positive (purple) |
| 16s rDNA sequencing and sequence alignment results | 16s rDNA is as listed in SEQ ID NO: 3; 99% homology with *Kurthia gibsonii* | 16s rDNA is as listed in SEQ ID NO: 4; 99% homology with *Clostridium kogasensis* | 16s rDNA is as listed in SEQ ID NO: 5; 99% homology with *Clostridium acidisoli* |
| Strain identification results | *Kurthia gibsonii* | *Clostridium kogasensis* | *Clostridium acidisoli* |

Inducted Acclimation of EO-Degrading Potential Bacteria Strains

Inducted acclimation of EO-degrading potential bacteria strains may include inducted acclimation of ethylene oxide tolerance and inducted acclimation of ethylene oxide degradation ability.

Ethylene oxide tolerance acclimation may include: successively passaging the original strains with the potential for ethylene oxide degradation by steaking on a series of plates of acclimation medium for ethylene oxide tolerance containing a gradient of increasing ethylene oxide concentrations; after each passaging, incubating under 20-40° C. for 24 to 48 hours, and selecting a single colony with the largest radius for the next passaging; and finally selecting a single colony with the largest colony radius on the acclimation medium plate containing the highest concentration of ethylene oxide (e.g., 500-800 mg/L) to obtain a predominant strain of ethylene oxide tolerance.

In some of these examples, the acclimation method described above includes: streaking the purified EO-degrading potential original strains in an ethylene oxide tolerance acclimation medium containing 100 mg/L ethylene oxide, respectively, and incubating under 20-40° C. for 24-48 h; selecting the single colony with the largest colony radius on each plate and subculturing to the ethylene oxide tolerance acclimation medium containing 100-200 mg/L ethylene oxide, respectively, and incubating under 20-40° C. for 24-48 h; selecting the single colony with the largest colony radius on each plate and subculturing to the ethylene oxide tolerance acclimation medium containing 200-500 mg/L ethylene oxide. 48 h; selecting the single colony with the largest colony radius on each plate and subculturing to the ethylene oxide tolerance acclimation medium containing 500-800 mg/L ethylene oxide, respectively, and incubating under 20-40° C. for 24-48 h; and, selecting the single colony with the largest colony radius on each plate containing 500-800 mg/L to obtain predominant strains of ethylene oxide tolerance.

In some of these examples, the above-mentioned ethylene oxide tolerance acclimation medium may be consisted of the following: peptone 10 g/L, glucose 40 g/L, agar 15 g/L, and ethylene oxide 100-800 mg/L, with a pH of 5.4-5.8.

In some of these examples, the preparation method of the above-mentioned ethylene oxide tolerance acclimation medium may be as follows: weighing, by mass, 10 parts of peptone, 40 parts of glucose, and 15 parts of agar, mixing in distilled water, adjusting the pH to 5.4-5.8, and bringing the volume to 1000 parts with distilled water; sterilizing; and injecting liquid ethylene oxide with a sealed injection syringe before use to make an ethylene oxide tolerance acclimation culture medium plate with 100-800 mg/L of ethylene oxide.

In some of these examples, the preparation method of ethylene oxide tolerance acclimation medium may be as follows: taking peptone 10 g, glucose 40 g, and agar 15 g to mix in distilled water, adjusting the pH to 5.4-5.8, and bringing the volume to 1000 mL with distilled water; dividing the medium into portions of 250 mL and sterilizing at 121° C. for 20 min; and, before use, heating the medium to melt, allowing to cool to about 50-56° C., and injecting 25-200 mg of ethylene oxide by a sealed syringe to make ethylene oxide tolerance acclimation medium with ethylene oxide of 100-800 mg/L.

In some of these examples, the concentrations of ethylene oxide in the ethylene oxide tolerance acclimation medium may be 100 mg/L, 200 mg/L, 500 mg/L, or 800 mg/L.

Inducted acclimation toward ethylene oxide degradability may include: successively passaging the predominant strain of ethylene oxide tolerance by steaking on a series of plates of acclimation medium for ethylene oxide degradation containing a high concentration of ethylene oxide e (e.g., 500-800 mg/L) and a gradient of decreasing proportion of carbon source; after each passaging, incubating under 20-40° C. for 24 to 48 hours, and selecting a single colony with the largest radius for the next passaging; and finally selecting a single colony with the largest colony radius on the acclimation medium plate containing the high concentration of ethylene oxide (e.g., 500-800 mg/L) and 0% of carbon source to obtain predominant strains of ethylene oxide tolerance and degradation.

In some of these examples, the predominant strains for ethylene oxide tolerance obtained by acclimation of ethylene oxide tolerance may be inoculated into plates with the acclimation medium of ethylene oxide degradation containing 800 mg/L ethylene oxide and 50% carbon source, respectively, and incubating under 20-40° C. for 24-48 h; selecting the single colony with the largest colony radius on each plate and subculturing to the plates of ethylene oxide degrading acclimation medium containing 800 mg/L ethylene oxide and 30% carbon source, respectively, and incubating under 20-40° C. for 24-48 h; selecting the single colony with the largest colony radius on the plate and subculturing to the plates of ethylene oxide degrading acclimation medium containing 800 mg/L ethylene oxide and 10% carbon source, respectively, and incubating under 20-40° C. for 24-48 h; selecting the single colony with the largest colony radius on the plate and subculturing to the plates of ethylene oxide degrading acclimation medium containing 800 mg/L ethylene oxide and 0% carbon source, respectively, and incubating under 20-40° C. for 24-48 h; and finally, selecting the single colony with the largest colony radius on the plates of ethylene oxide degrading acclimation medium containing 800 mg/L ethylene oxide and 0% carbon source, to obtain the predominant strains for tolerance and degradation of ethylene oxide.

In some of these examples, the ethylene oxide degradation acclimation medium may be consisted of the following: peptone 10 g/L, glucose 0-20 g/L, agar 15 g/L, and ethylene oxide 800 mg/L, with a pH of 5.4-5.8.

In some of these examples, the preparation method of the ethylene oxide degradation acclimation medium may be as follows: weighing, by mass, 10 parts of peptone by mass, 0-20 parts of glucose, and 15 parts of agar, mixing in distilled water, adjusting the pH to 5.4-5.8, and bringing the volume to 1000 parts with distilled water; sterilizing; and injecting liquid ethylene oxide with a sealed injection syringe before use to make an ethylene oxide degradation acclimation culture medium plate containing 0%-50% carbon source and 800 mg/L of ethylene oxide.

In some of these examples, the preparation method of the ethylene oxide degradation acclimation medium may be as follows: taking peptone 10 g, glucose 0-20 g, and agar 15 g to mix in distilled water, adjusting the pH to 5.4-5.8, and bringing the volume to 1000 mL with distilled water; dividing the medium into portions of 250 mL and sterilizing at 121° C. for 20 min; and, before use, heating the medium to melt, allowing to cool to about 50-56° C., and injecting 200 mg of liquid ethylene oxide with a sealed injection syringe to make ethylene oxide degradation acclimation medium plate contain 0%-50% carbon source and 800 mg/L ethylene oxide.

In some of these examples, the glucose concentrations in the ethylene oxide degradation acclimation medium may be 20 g/L, 12 g/L, 4 g/L, and 0 g/L, respectively corresponding to carbon source of 50%, 30%, 10%, and 0% in the ethylene oxide degradation acclimation medium.

The following is an exemplary example of inducted acclimation of EO-degrading potential bacteria strains.

EXAMPLE 2

Phase I: Inducted Acclimation of Ethylene Oxide Tolerance

Four tolerance acclimation medium with different EO concentrations were prepared as follows: taking peptone 10 g, glucose 0-20 g, and agar 15 g to mix in distilled water, adjusting the pH to 5.4-5.8, and bringing the volume to 1000 mL with distilled water; dividing the medium into portions of 250 mL and sterilizing at 121° C. for 20 min; and, before use, heating the medium to melt, allowing to cool to about 50-56° C., and injecting 25 mg, 50 mg, 125 mg or 200 mg of liquid ethylene oxide with a sealed injection syringe to make four ethylene oxide degradation acclimation plates with different EO concentrations (100 mg/L, 200 mg/L, 500 mg/L or 800 mg/L), designated as ethylene oxide tolerance acclimation medium A, B, C, and D.

Using the method of plate streaking, the three EO-degrading potential strains of the EO-06 original strain, EO-08 original strain and EO-09 original strain were inoculated onto the tolerance acclimation medium A and incubated at a constant temperature of 37° C. for 48 h. Then the single colony with the largest radius on each plate was selected and subcultured onto the tolerance acclimation medium B and incubated at 37° C. for 48 h. Again, the single colony with the largest colony radius on each plate was selected and subcultured onto the tolerance acclimation medium C and incubated at a constant temperature of 37° C. for 48 h. The single colony with the largest radius on each plate was selected and subcultured onto the tolerance acclimation medium D and incubated at a constant temperature of 37° C. for 48 h. Then the single colony with the largest colony radius on each plate was selected to further obtain three strains with tolerance against ethylene oxide corresponding to the EO-06 original strain, EO-08 original strain and EO-09 original strain, respectively.

Phase II: Inducted Acclimation of Ethylene Oxide Degradation Ability

Four ethylene oxide degradation acclimation mediums with different carbon source % were prepared as follows: taking peptone 10 g, glucose (20 g, 12 g, 4 g or 0 g), and agar 15 g to mix in distilled water, adjusting the pH to 5.4-5.8, and bringing the volume to 1000 mL with distilled water; dividing the medium into portions of 250 mL and sterilizing at 121° C. for 20 min; and, before use, heating the medium to melt, allowing to cool to about 50-56° C., and injecting 200 mg of liquid ethylene oxide with a sealed injection syringe to make four ethylene oxide degradation acclimation medium plates with different carbon source % (50%, 30%, 10%, and 0%), designated as ethylene oxide degradation acclimation medium A, B, C, and D.

Using the method of plate streaking, the three EO-degrading potential strains, i.e., the EO-06 original strain, EO-08 original strain and EO-09 original strain, were inoculated onto the degradation acclimation medium A and incubated at a constant temperature of 37° C. for 48 h. Then the single colony with the largest radius on each plate was selected and subcultured onto the degradation acclimation medium B and incubated at 37° C. for 48 h. Again, the single colony with the largest colony radius on each plate was selected and subcultured onto the degradation acclimation medium C and incubated at a constant temperature of 37° C. for 48 h. The single colony with the largest radius on each plate was selected and subcultured onto the degradation acclimation medium D and incubated at a constant temperature of 37° C. for 48 h (except for EO-08, which did not grow on medium C). Then the single colony with the largest colony radius on each plate was selected respectively to further obtain three strains with tolerance and degradation ability of high-concentration ethylene oxide corresponding to the EO-06 original strain, and EO-09 original strain, which were stored on bevels made from agar medium containing nutrients corresponding to the ethylene oxide degradation acclimation medium D.

The results of inducted acclimation of ethylene oxide tolerance and degradation capacity are summarized in Table 2. The results in Table 2 show that the EO-06 and EO-09 strains after acclimation described above were able to grow normally under the culture conditions with ethylene oxide as the only carbon source and use ethylene oxide as a carbon source. EO-08 was not able to grow normally under the culture condition with ethylene oxide as the only carbon source, but was able to grow with additional carbon source of 30% or above.

1000 mL with water in volume and adjusting the pH to 5.4-5.8; dividing the medium into portions of 250 mL in 500 mL Erlenmeyer flasks, sterilizing at 121° C. for 20 min, and allowing to cool to room temperature; injecting 160 mg or 320 mg of ethylene oxide with a sealed syringe to make two kinds of liquid Sabouraud induction medium containing different ethylene oxide concentrations (400 mg/L and 800 mg/L).

Two types of liquid Sabouraud induction medium for EO-06 and EO-09 with different ethylene oxide concentrations were made as follows: adding 10 g peptone to distilled water, bringing the volume to 1000 mL, mixing thoroughly; dividing into 400 mL portions, sterilizing at 121° C. for 20 min, and allowing to cool to room temperature for storage; injecting 160 mg or 320 mg of ethylene oxide with a sealed syringe to make two kinds of liquid Sabouraud induction medium containing different ethylene oxide concentrations (400 mg/L and 800 mg/L).

The microbes were cultured and activated by taking 10 μL each of the original EO-06, EO-08, and EO-09 EO-degrading potential strains obtained from Example 1 without induced acclimation and the EO-06, EO-08, and EO-09 strains after induced acclimation obtained from Example 2, inoculating on 100 μL of 10 μL, respectively and cultured for 48 h (37° C., 200 rpm) to obtain activated mixture of the EO-06, EO-08, EO-09 original strains and of the EO-06, EO-08, EO-09 strains after induced acclimation. The cell count in the culture mixture was $10^{10}$-$10^{12}$ cfu/mL.

TABLE 2

Results of induced acclimation of ethylene oxide tolerance and degradation ability

| | Phase I | | | | Phase II | | | |
|---|---|---|---|---|---|---|---|---|
| Carbon source (%) | 100 | 100 | 100 | 100 | 50 | 30 | 10 | 0 |
| EO concentration (mg/L) | 100 | 200 | 500 | 800 | 800 | 800 | 800 | 800 |
| EO-06 growth | + | + | + | + | + | + | + | + |
| EO-08 growth | + | + | + | + | + | + | − | − |
| EO-09 growth | + | + | + | + | + | + | + | + |

The EO-06, EO-08 and EO-09 strains after the inducted acclimation were subjected to the morphological characterization, physiological and biochemical characterization, and molecular biology characterization the same as in Example 1. The results show that the Strain EO-06 after the inducted acclimation was *Kurthia gibsonii*, the Strain EO-08 after the inducted acclimation was *Clostridium kogasensis*, and the strain EO-09 after the inducted acclimation was *Clostridium acidisoli*.

The *Kurthia gibsonii* strain EO-06, the *Clostridium kogasensis* strain EO-08, and the *Clostridium acidisoli* strain EO-09 after the inducted acclimatization were deposited with the deposit numbers being CGMCC No. 18436, CGMCC No. 18438, and CGMCC No. 18439 respectively.

Comparative Experiment of Degradation of Ethylene Oxide

In the example below, comparative experiments were conducted to test the ability of the *Kurthia gibsonii* strain EO-06, the *Clostridium kogasensis* strain EO-08, and the *Clostridium acidisoli* strain EO-09 after the inducted acclimatization to degrade ethylene oxide.

EXAMPLE 3

I. Experimental Method:

Liquid Sabouraud medium for EO-08 was made as follows: taking 12 g of glucose and 10 g of peptone, bring to To conduct a comparative experiment of ethylene oxide degradation, the following treatment and control groups were incubated in a 37° C. incubator for 48 hours.

Experimental group 1A (acclimated strains/800 mg/L ethylene oxide): 5 mL each of the activated mixture of the EO-06, EO-08, Strain EO-09s after induced acclimation was inoculated in 400 mL of the liquid Sabouraud induction medium containing 800 mg/L ethylene oxide, with cell count in the medium being $10^8$-$10^{10}$ cfu/mL;

Experimental group 1B (unacclimated original strain/800 mg/L ethylene oxide): 5 mL each of the activated mixture of the EO-06, EO-08, EO-09 original strains before induced acclimation was inoculated in 400 mL of the liquid Sabouraud induction medium containing 800 mg/L ethylene oxide, with cell count in the medium being $10^8$-$10^{10}$ cfu/mL;

Control group 1: Liquid Sabouraud induction medium containing 800 mg/L of ethylene oxide without inoculation of any strain;

Experimental group 2A (acclimated strains/400 mg/L ethylene oxide): 5 mL each of the activated mixture of the EO-06, EO-08, Strain EO-09s after induced acclimation was inoculated in 400 mL of the liquid Sabouraud induction medium containing 400 mg/L ethylene oxide, with cell count in the medium being $10^8$-$10^{10}$ cfu/mL;

Experimental group 2B (unacclimated original strain/400 mg/L ethylene oxide): 5 mL each of the activated mixture of the EO-06, EO-08, EO-09 original strains before induced acclimation was inoculated in 400 mL of the liquid Sabouraud induction medium containing 400 mg/L ethylene oxide, with cell count in the medium being $10^8$-$10^{10}$ cfu/mL; and Control group 2: Liquid Sabouraud induction medium containing 400 mg/L of ethylene oxide without inoculation of any strain.

To calculate the concentrations of residual ethylene oxide and the degradation rates, samples were taken from the above Treatment groups and Control groups after the comparative test for gas chromatography analysis according to the methods described in "*Sanitary Standards for Disposable Hygiene Products*" (GB15979-2002) of China National Standards as follows:

a series of ethylene oxide standards of 0-200 mg/L concentrations were made by taking a certain volume of pure ethylene oxide gas with a sealed syringe for dissolving in deionized water;

the subject samples to be analyzed were prepared by diluting samples from the treatment and control groups 5 times with deionized water;

after the GC instrument is stabilized and under the same conditions, 2 μL each of the ethylene oxide standards and the diluted samples to be analyzed were injected into the GC instrument, wherein each sample was measured twice in parallel;

qualitative determination was conducted according to the retention time and quantitative calculation on each peak area was performed to take the average value;

an ethylene oxide standard curve was plotted according to the measurement data of the ethylene oxide standards, and the concentrations of residual ethylene oxide within each sample from the control and treatment groups were found based on the peak area corresponding to ethylene oxide thereof; and the degradation rate of ethylene oxide for each sample was calculated according to the following formula: Degradation Rate (%)=(Control Group Concentration−Treatment Group Concentration)/Control Group Concentration×100; specifically, the degradation rates of Treatment groups 1 and 2 were calculated based on Control Group 1, while those of Treatment groups 3 and 4 calculated based on Control Group 2.

Other details of the experiment include Column: Chromosorb 101HP60-80 mesh, glass column 2 m long, diameter 3 mm Column temperature: 120° C. Detector: 150° C., Gasifier: 150° C.; Carrier gas volume: Nitrogen: 35 ml/min, Hydrogen: 35 ml/min, Air: 350 ml/min, and the pre-column pressure is about 108 Kpaa.

Additionally, promotion in the degradation ability for ethylene oxide of the strain before and after acclimation was calculated according to the following formula:

Promotion of degradation ability (%)=(Degradation Rate (%) of the strain after acclimation−Degradation Rate (%) of the strain before acclimation).

II. Experimental Results

The experimental results are summarized in Table 3 and also shown in FIGS. 4A-6B. It can be seen from Table 3 that the original strains of *Kurthia gibsonii* EO-06, *Clostridium kogasensis* EO-08, and *Clostridium acidisoli* EO-09 after induced acclimation were able to obtain outstanding tolerance and significant degradation ability against high concentrations of ethylene oxide, capable of degrading high concentrations of ethylene oxide with no or low carbon source.

Specifically, the degradation rates of EO-06, EO-08, and EO-09 strains after acclimation of 400 mg/L of ethylene oxide were 80.85%, 83.61%, and 84.19%, which were higher than the original strains before acclimation by 340.60%, 338.67%, and 326.71%, respectively. The degradation rates of EO-06, EO-08, and EO-09 strains after acclimation for 800 mg/L of ethylene oxide were 67.82%, 91.70%, and 51.64%, which were higher than the original strains before acclimation by 620.72%, 392.48% and 752.1%, respectively.

TABLE 3

Comparative experiment results of ethylene oxide degradation of EO-06, EO-08 and EO-09 strains before and after inducted acclimation.

| Strain | EO concentration before test (mg/L) | EO concentration after test (mg/L) | | | Degradation rate (%) | | Promotion of degradation ability (%) |
|---|---|---|---|---|---|---|---|
| | | Before acclimation | After acclimation | Control | Before acclimation | After acclimation | |
| EO-06 | 800 | 464.2 | 164.9 | 512.4 | 9.41% | 67.82% | 620.72% |
| | 400 | 181.6 | 42.6 | 222.4 | 18.35% | 80.85% | 340.60% |
| EO-08 | 800 | 423.6 | 43.2 | 520.5 | 18.62% | 91.70% | 392.48% |
| | 400 | 203.4 | 41.2 | 251.3 | 19.06% | 83.61% | 338.67% |
| EO-09 | 800 | 567.6 | 292.2 | 604.2 | 6.06% | 51.64% | 752.1% |
| | 400 | 186.3 | 36.7 | 232.1 | 19.73% | 84.19% | 326.71% |

EXAMPLE 4

Treatment of Ethylene Oxide Sterilization Waste Gas

In general, ethylene oxide sterilization waste gas can be absorbed into water. The water containing the absorbed ethylene oxide can be contacted with a strain of the present invention in a method of biodegrading ethylene oxide. The water containing the absorbed ethylene oxide can be discharged or transferred to an anaerobic vessel, such as an anaerobic sewage tank. A strain of the present invention can then be added to the tank, thereby biodegrading the ethylene oxide.

In particular, 1) after the ethylene oxide sterilizer has sterilized, the ethylene oxide sterilization exhaust gas generated is fed into a hydration system, which uses the internal circulating water to absorb the incoming ethylene oxide sterilization exhaust gas, and several cycles of absorption produce ethylene oxide wastewater containing 253.48 mg/L of ethylene oxide.

(2) The wastewater was passed into an anaerobic ethylene oxide treatment cell inoculated with mixed EO-06, EO-08, and EO-09 strains, and the strain concentration was $10^{10}$-$10^{12}$ cfu/mL, the inoculation amount was 1%-2%, the strain(s) used the active sludge in the anaerobic ethylene oxide treatment cell as the culture, ethylene oxide was used as the carbon source and energy for metabolism, growth and proliferation, thus achieving the purpose of ethylene oxide treatment.

The mixture in the treatment cell was continuously stirred, the temperature was controlled at 32° C.-42° C. and the treatment time was 48 hours. The wastewater was treated in the anaerobic biological ethylene oxide treatment cell inoculated with the strain(s), and the residual concentration of ethylene oxide in the treated wastewater was 18.33 mg/L with a treatment efficiency of 92.77%.

The above concentrations were detected by gas chromatography in accordance with GB 15979-2002 (Appendix D), which is explained above. The degradation rate was calculated according to the following formula: Degradation rate= (starting concentration−residual concentration)/starting concentration.

As another practical application, activated sludge can be contacted with a strain of the present invention, thereby biodegrading ethylene oxide in the activated sludge.

Comparative tests and applications may be carried out in other samples containing ethylene oxide, such as sewage, sludge, exhaust gas, or wastewater, such as industrial (including industries related to petroleum and derivative products), medical treatment (such as ethylene oxide sterilant) and other sewage, sludge, exhaust gas, or wastewater using strains of the invention In the above-described tests and applications, the degradation rate is at least 10%, 15%, 20%, 25%, 30%, 35%, 40%, 50%, 60%, 70%, 75%, 80%, 90%, 95%, 100%, 125%, 150%, 200%, 250%, 300%, 350%, 400%, 450%, 500%, 550%, 600%, 650%, 700%, 750%, 800%, 850%, 900%, 1000%, 1100%, 1200%, 1300%, 1400%, or 1500% greater relative to the degradation rate of ethylene oxide in the absence of the *Kurthia gibsonii* strain EO-06; the *Clostridium kogasensis* strain EO-08; the *Clostridium acidisoli* strain EO-09, a *Kurthia gibsonii* strain comprising the 16S rDNA sequence of SEQ ID NO: 3; a *Clostridium kogasensis* strain comprising the 16S rDNA sequence of SEQ ID NO: 4; or a *Clostridium acidisoli* strain comprising the 16S rDNA sequence of SEQ ID NO: 5.

The detailed embodiments described herein are only for the purpose of illustrating the present disclosure, and are not intended to limit the scope of the present disclosure in any way. It would be understood by a person skilled in the art that various changes and modifications can be made to the embodiments described herein without departing from the scope and spirit of the present disclosure. Such changes and modifications are contemplated by the present disclosure, the scope of which should only be defined by the following claims.

What is claimed is:

1. A product selected from the group consisting of:
   a strain for degrading ethylene oxide, which is *Kurthia gibsonii* EO-06 with Deposit Number of CGMCC No. 18436;
   a strain for degrading ethylene oxide, which is *Clostridium kogasensis* strain EO-08 with Deposit Number of CGMCC No. 18438;
   a strain for degrading ethylene oxide, which is *Clostridium acidisoli* strain EO-09 with Deposit Number of CGMCC No. 18439; and
   a degradation agent for degrading ethylene oxide, comprising two or more strains selected from the group consisting of a *Kurthia gibsonii* strain EO-06 with Deposit Number of CGMCC No. 18436, a *Clostridium kogasensis* strain EO-08 with Deposit Number of CGMCC No. 18438 and a *Clostridium acidisoli* strain EO-09 with Deposit Number of CGMCC No. 18439.

2. The product according to claim 1, wherein the degradation agent is prepared by culturing the two or more strains.

3. The product according to claim 1, wherein a final concentration of the two or more strains in the degradation agent is at least $10^8$ cfu/mL.

4. A method for preparing a degradation agent for degrading ethylene oxide, the method selected from the group consisting of:
   i) incubating one or more strains selected from the group consisting of a *Kurthia gibsonii* strain EO-06 with Deposit Number of CGMCC No. 18436, a *Clostridium kogasensis* strain EO-08 with Deposit Number of CGMCC No. 18438 and a *Clostridium acidisoli* strain EO-09 with Deposit Number of CGMCC No. 18439 in a liquid Sabouraud medium and at a temperature of 20-40° C.;
   ii) a) inducing acclimation for ethylene oxide tolerance, comprising: successively passaging the bacteria with ethylene oxide degradation potential by streaking the same on a series of acclimation medium for ethylene oxide tolerance containing a gradient of increasing ethylene oxide concentrations from 100 to 800 mg/L; after each passaging, incubating at 20-40° C. for 24 to 48 hours, and selecting a single colony with a largest radius for next passaging; and finally selecting a single colony with a largest colony radius on an acclimation medium containing ethylene oxide of 500-800 mg/L to obtain a bacteria strain of ethylene oxide tolerance,
   wherein the series of acclimation medium for ethylene oxide tolerance have ethylene oxide concentrations increasing between 100 and 800 mg/L and comprises, by mass, 10 parts of peptone, 40 parts of glucose, and 15 parts of agar, which are mixed with water, adjusted to a pH of 5.4-5.8, and the volume brought to 1000 parts with water;
   and
   b) inducing acclimation for ethylene oxide degradation ability, comprising:
   successively passaging the bacteria strain of ethylene oxide tolerance by streaking the same on a series of acclimation medium for ethylene oxide degradation containing ethylene oxide of 500-800 mg/L and a gradient of decreasing proportion of carbon source from 50% to 0%; after each passaging, incubating at 20-40° C. for 24 to 48 hours, and selecting a single colony with a largest radius for next passaging; and finally selecting a single colony with a largest colony radius on the acclimation medium containing 500-800 mg/L of ethylene oxide and minimal carbon source to obtain the bacteria strain having ethylene oxide tolerance and degradation ability;
   wherein the series of acclimation medium for ethylene oxide degradation have an ethylene oxide concentration of 500-800 mg/L and comprises, by mass, 10 parts of peptone, glucose decreasing from 20 parts to 0 parts, and agar 15 parts, which are mixed with water, adjusted to a pH of 5.4-5.8, and the volume brought to 1000 parts with water; and
   iii) a) collecting microbial active sludge mixture containing ethylene oxide;
   b) mixing the sludge mixture with phosphate buffer, clarifying and filtering to obtain a suspension;
   c) incubating the suspension in an enriched medium containing ethylene oxide at a temperature of 20-40° C., to obtain a bacterial suspension capable of surviving in an environment containing ethylene oxide
   wherein, the enriched medium containing ethylene oxide has an ethylene oxide concentration of 100 mg/L and comprises, by mass, 40 parts of glucose and 10 parts peptone, which are brought to 1000 parts with water in volume and adjusted to a pH of 5.4-5.8;
   and
   d) incubating the bacterial suspension in a screening and purification medium containing ethylene oxide at a temperature of 20-40° C. to obtain the bacteria with potential of ethylene oxide degradation;
   wherein the screening and purification medium containing ethylene oxide has an ethylene oxide concentration of 100 mg/L and comprises, by mass, 40 parts of glucose, 10 parts of peptone, and 15 parts agar which are brought to 1000 parts with water in volume and adjusted to a pH of 5.4-5.8.

5. The method according to claim 4, wherein the liquid Sabouraud medium comprises: by mass, 40 parts of glucose and 10 parts peptone, which are brought to 1000 parts with water in volume and adjusted to a pH of 5.4-5.8.

6. A method for biodegrading ethylene oxide or decreasing the amount of ethylene oxide in sample, comprising a method selected from the group consisting of:
   i) degrading ethylene oxide with one or more strains selected from the group consisting of a *Kurthia gibsonii* strain EO-06 with Deposit Number of CGMCC No. 18436, a *Clostridium* kogasensis strain EO-08 with Deposit Number of CGMCC No. 18438 and a *Clostridium acidisoli* strain EO-09 with Deposit Number of CGMCC No. 18439; and
   ii) a) adding to a sample comprising ethylene oxide an amount a pure culture of a *Kurthia gibsonii, Clostridium kogasensis*, or *Clostridium acidisoli* strain bacterium,
   b) allowing the bacterium to degrade the ethylene oxide, thereby decreasing the amount of ethylene oxide, wherein the 16S rDNA sequence of the *Kurthia gibsonii* strain bacterium is SEQ ID NO. 3; the 16S rDNA sequence of the *Clostridium* kogasensis strain bacterium is SEQ ID NO. 4; or the 16S rDNA sequence of the *Clostridium acidisoli* strain bacterium is SEQ ID NO. 5.

7. The method according to claim 6, wherein the method is used to degrade ethylene oxide in waste gas or waste water and comprises mixing the waste gas or waste water with one or more strains selected from the group consisting of a *Kurthia gibsonii* strain EO-06 with Deposit Number of CGMCC No. 18436, a *Clostridium* kogasensis strain EO-08 with Deposit Number of CGMCC No. 18438 and a *Clostridium acidisoli* strain EO-09 with Deposit Number of CGMCC No. 18439.

8. The method of claim 6, wherein the degrading ethylene oxide with one or more strains selected from the group consisting of a *Kurthia gibsonii* strain EO-06 with Deposit Number of CGMCC No. 18436, a *Clostridium* kogasensis strain EO-08 with Deposit Number of CGMCC No. 18438 and a *Clostridium acidisoli* strain EO-09 with Deposit Number of CGMCC No. 18439 comprises:
  incubating the one or more strains in a liquid Sabouraud medium and at a temperature of 20-40° C. for 24 to 48 hours to obtain a culture of the one or more strains; and
  degrading the ethylene oxide with the culture of the one or more strains.

9. The method according to claim 6, wherein the degradation rate is at least 10% greater relative to the degradation rate of ethylene oxide in the absence of the strain for degrading ethylene oxide.

10. The method according to claim 6, wherein the strain for degrading ethylene oxide ranges in concentration from $10^8$ cfu/mL to $10^{10}$ cfu/mL.

11. The method according to claim 6, wherein the *Kurthia gibsonii*, *Clostridium kogasensis*, or *Clostridium acidisoli* strain bacterium is capable of using ethylene oxide as a carbon source and is capable of growing normally with ethylene oxide as the carbon source in the culture.

12. The method according to claim 6, wherein the *Kurthia gibsonii* strain bacterium is *Kurthia gibsonii* EO-06 with Deposit Number of CGMCC No. 18436, the *Clostridium* kogasensis strain bacterium is *Clostridium* kogasensis strain EO-08 with Deposit Number of CGMCC No. 18438 and the *Clostridium acidisoli* strain bacterium is *Clostridium acidisoli* strain EO-09 with Deposit Number of CGMCC No. 18439.

* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic construct

<400> SEQUENCE: 1
agagtttgat cctggctcag                                                    20

<210> SEQ ID NO 2
<211> LENGTH: 19
<212> TYPE: DNA
<213> ORGANISM: Artificial Sequence
<220> FEATURE:
<223> OTHER INFORMATION: Synthetic construct

<400> SEQUENCE: 2
ggttaccttg ttacgactt                                                     19

<210> SEQ ID NO 3
<211> LENGTH: 1430
<212> TYPE: DNA
<213> ORGANISM: Kurthia gibsonii

<400> SEQUENCE: 3
ctatacatgc agtcgagcga atgacgagaa gcttgcttct ctgatttagc ggcggacggg         60
tgagtaacac gtgggcaacc tgccctacag atcgggataa ctcagggaaa cctggctaa         120 taccggataa tccttcgaat cacatgtttt gaagttgaaa ggcgcttcgg cgtcactgta        180
ggatgggccc gcggtgcatt agctagttgg tggggtaacg gcctaccaag gcaacgatgc        240
atagccgacc tgagagggtg atcggccaca ttgggactga gacacggccc aaactcctac        300
```

-continued

```
gggaggcagc agtagggaat cttccacaat ggacgaaagt ctgatggagc aacgccgcgt        360
gagtgatgaa ggttttcgga tcgtaaaact ctgttgtaag ggaagaacaa gtacgttagg        420
aaatgaacgt accttgacgg taccttatta gaaagccacg gctaactacg tgccagcagc        480
cgcggtaata cgtaggtggc aagcgttgtc cggatttatt gggcgtaaag cgcgcgcagg        540
tggtttctta agtctgatgt gaaagcccac ggctcaaccg tggagggtca ttggaaactg        600
gggaacttga gtgcagaaga ggatagtgga attccaagtg tagcggtgaa atgcgtagag        660
atttggagga acaccagtgg cgaaggcgac tgtctggtct gtaactgaca ctgaggcgcg        720
aaagcgtggg gagcaaacag gattagatac cctggtagtc cacgccgtaa acgatgagtg        780
ctaagtgtta gggggtttcc gccccttagt gctgcagcta acgcattaag cactccgcct        840
ggggagtacg accgcaaggt tgaaactcaa aggaattgac gggggcccgc acaagcggtg        900
gagcatgtgg tttaattcga agcaacgcga agaaccttac caggtcttga catcccaatg        960
accgtcctag agataggatt ttcccttcgg ggacattggt gacaggtggt gcatggttgt       1020
cgtcagctcg tgtcgtgaga tgttgggtta agtcccgcaa cgagcgcaac ccttattctt       1080
agttgccatc atttagttgg gcactctaag gagactgccg gtgacaaacc ggaggaaggt       1140
ggggatgacg tcaaatcatc atgcccctta tgacctgggc tacacacgtg ctacaatgga       1200
cgatacaaag agtcgcaaac tcgcgagggt aagctaatct cataaaatcg ttctcagttc       1260
ggattgtagg ctgcaactcg cctgcatgaa gccggaatcg ctagtaatcg cggatcagca       1320
tgccgcggtg aatacgttcc cgggccttgt acacaccgcc cgtcacacca cgagagtttg       1380
taacacccga gtcggtgggg taaccgtaa ggagccagcc gctaagtgaa                   1430
```

<210> SEQ ID NO 4
<211> LENGTH: 1401
<212> TYPE: DNA
<213> ORGANISM: Clostridium kogasensis

<400> SEQUENCE: 4

```
cggcagctac acatgcaagt cgagcgatga atcccttcg gggatggatt agcggcggac          60
gggtgagtaa cacgtgggca acctgcctca aagtgggggga tagcctcccg aaagggagat       120
taataccgca taatgttaga tcttcacatg aagaactaat taaggagca atccgctttg         180
agatgggccc gcggcgcatt agctagttgg tgaggtaatg gctcaccaag gcgacgatgc         240
gtagccgacc tgagagggtg atcggccaca ttggaactga gacacggtcc agactcctac         300
gggaggcagc agtggggaat attgcacaat ggggggaaacc ctgatgcagc aacgccgcgt       360
gagtgatgaa ggtcttcgga ttgtaaagct ctgtcttttg gacgataat gacggtacca         420
aaggaggaag ccacggctaa ctacgtgcca gcagccgcgg taatacgtag gtggcgagcg         480
ttgtccggat ttactgggcg taaagggtgc gtaggcggat atttaagtgg gatgtgaaat         540
acccgggctc aacttgggtg ctgcattcca aactggatat ctagagtgcg ggagaggaga         600
gtggaattcc tagtgtagcg gtgaaatgcg tagagattag gaagaacacc agtggcgaag         660
gcgactctct ggaccgtaac tgacgctgag gcacgaaagc gtgggagca acaggatta          720
gataccctgg tagtccacgc cgtaaacgat gaatactagg tgtaggaggt atcgacccct        780
tctgtgccgc agttaacaca ataagtattc gcctgggga gtacggtcgc aagattaaaa        840
ctcaaaggaa ttgacggggg cccgcacaag cagcggagca tgtggtttaa ttcgaagcaa        900
cgcgaagaac cttacctaga cttgacatac cctgaattac cggtaatgcg ggaagccctt        960
cgggcaggg atacaggtgg tgcatggttg tcgtcagctc gtgtcgtgag atgttaggtt        1020
```

```
aagtcctgca acgagcgcaa ccctattat tagttgctac cattaagttg agcactctag    1080
taagactgcc tgggttaacc aggaggaagg cggggatgac gtcaaatcat catgcccctt    1140
atgtctaggg ctacacacgt gctacaatgg gcggtacaaa aagatgcaaa ctcgcgagag    1200
tgagccaaac tttaaaaccg cccccagttc ggattgtagg ctgaaactcg cctacatgaa    1260
gccggagttg ctagtaatcg cgaatcagca tgtcgcggtg aatacgttcc cgggccttgt    1320
acacaccgcc cgtcacacca tgagagctgg caacacccga agtccgtgag gtaaccgtaa    1380
ggagccagcg gccgaagtgg g                                              1401

<210> SEQ ID NO 5
<211> LENGTH: 1432
<212> TYPE: DNA
<213> ORGANISM: Clostridium acidisoli

<400> SEQUENCE: 5
agagtttgat catggctcag gacgaacgct ggcggcgtgc ttaacacatg caagtcgagc      60
gagaaacctt cgggttttcta gcggcggacg ggtgagtaac acgtgggtaa cctgcctcaa    120
agtgggggat agccttccga aggaagatt aataccgcat aacattgtag cttcgcatga     180
agcaacaatt aaaggagtaa tccgctttga gatggacccg cggcgcatta gctagttgga    240
gaggtaacgg ctcaccaagg cgacgatgcg tagccgacct gagagggtga tcggccacat    300
tggaactgag acacggtcca gactcctacg ggaggcagca gtggggaata ttgcacaatg    360
ggcgaaagcc tgatgcagca acgccgcgtg agtgatgaag gtcttcggat tgtaaagctc    420
tgtcttttgg gacgataatg acggtaccaa aggaggaagc cacggctaac tacgtgccag    480
cagccgcggt aatacgtagg tggcaagcgt tgtccggaat tactgggcgt aaaggatgtg    540
taggcggata tttaagtgag atgtgaaatc cccgagctca acttggggc tgcatttcaa     600 actgggtatc tagagtgcag gagaggaaag cggaattcct agtgtagcgg tgaaatgcgt    660
agagattagg aagaacatca gtggcgaagg cggctttctg gactgtaact gacgctgagg    720
catgaaagcg tggggagcaa acaggattag ataccctggt agtccacgcc gtaaacgatg    780
agtactaggt gtaggaggta tcgactcctt ctgtgccgca gttaacacaa taagtactcc    840
gcctgggaag tacggtcgca agattaaaac tcaaaggaat tgacggggc ccgcacaagc     900 agcggagcat gtggtttaat tcgaagcaac gcgaagaacc ttacctagac ttgacatccc    960
ctgaataacg tagagatacg cgaagccctt cggggcaggg agacaggtgg tgcatggttg   1020
tcgtcagctc gtgtcgtgag atgttgggtt aagtcccgca acgagcgcaa cccttatcat   1080
tagttgctac catttagttg agcactctag tgagactgcc cggttaacc gggaggaagg    1140 cggggatgac gtcaaatcat catgcccctt atgtctaggg ctacacacgt gctacaatgg   1200
tgagaacaac gagatgcaat accgcgaggt ggagcaaaac ttcaaaactc atctcagttc   1260
ggattgtagg ctgaaactcg cctacatgaa gttggagttg ctagtaatcg cgaatcagaa   1320
tgtcgcggtg aatacgttcc cgggccttgt acacaccgcc cgtcacacca tgagagctgg   1380
taacacccga agtccgtgag gtaacccttta ttggggccag cggccgaagg tg           1432
```